(12) United States Patent
Marquais-Bienewald et al.

(10) Patent No.: US 8,641,783 B2
(45) Date of Patent: Feb. 4, 2014

(54) DISULFIDE OR THIOL POLYMERIC HAIR DYES

(75) Inventors: Sophie Marquais-Bienewald, Hegenheim (FR); Christian Cremer, Lorrach (DE); Beate Frohling, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/816,527

(22) PCT Filed: Aug. 15, 2011

(86) PCT No.: PCT/EP2011/064022
§ 371 (c)(1),
(2), (4) Date: Feb. 12, 2013

(87) PCT Pub. No.: WO2012/022709
PCT Pub. Date: Feb. 23, 2012

(65) Prior Publication Data
US 2013/0139328 A1   Jun. 6, 2013

Related U.S. Application Data

(60) Provisional application No. 61/374,279, filed on Aug. 17, 2010, provisional application No. 61/485,127, filed on May 12, 2011.

(30) Foreign Application Priority Data

Aug. 17, 2010   (EP) .................................... 10173000
May 12, 2011   (EP) .................................... 11165787

(51) Int. Cl.
*A61Q 5/10*   (2006.01)

(52) U.S. Cl.
USPC ................ 8/405; 8/435; 8/551; 8/552; 8/555; 8/557; 8/559

(58) Field of Classification Search
USPC .............. 8/405, 435, 551, 552, 555, 557, 559
See application file for complete search history.

(56) References Cited

U.S. PATENT DOCUMENTS

| | | | |
|---|---|---|---|
| 4,182,612 A | 1/1980 | Sokol et al. | |
| 4,228,259 A | 10/1980 | Kalopissis et al. | |
| 5,935,560 A | 8/1999 | Super et al. | |
| 6,306,182 B1 | 10/2001 | Chan | |
| 7,731,761 B2 * | 6/2010 | Marquais-Bienewald et al. | 8/405 |

FOREIGN PATENT DOCUMENTS

| | | |
|---|---|---|
| EP | 1466583 A1 | 10/2004 |
| FR | 2456764 A | 12/1980 |
| FR | 2921256 A1 | 3/2009 |
| WO | 2007/072521 A1 | 6/2007 |
| WO | 2009/090121 A1 | 7/2009 |
| WO | 2009/090122 A2 | 7/2009 |

OTHER PUBLICATIONS

STIC Search Report dated Sep. 5, 2013.*
English language abstract of EP1466583 Oct. 13, 2004.
English language abstract of FR2456764 Dec. 12, 1980.
English language abstract of FR2921256 Mar. 27, 2009.

* cited by examiner

*Primary Examiner* — Eisa Elhilo
(74) *Attorney, Agent, or Firm* — Shiela A. Loggins

(57) ABSTRACT

The present invention relates to the reaction product of (A) a polymeric backbone with (B) A chromophore; and with (C) at least one sulfide containing compound. Very good dyeing results are obtained with this new technology.

23 Claims, No Drawings

DISULFIDE OR THIOL POLYMERIC HAIR DYES

This application is a 371 of PCT/EP2011/064022, filed Aug. 15, 2011 which takes the benefit of 61/485,127 filed May 12, 2011 and 61/374,279 filed Aug. 17, 2010.

The present invention relates to novel polymeric dyes referring to the reaction product of a polymeric back bone, a chromophore and a sulfide containing compound, hair dyeing compositions comprising these reaction products, to a process for their preparation and to their use for dyeing of organic materials, such as keratin-containing fibers, leather, silk, cellulose or polyamides, natural and synthetic fibers like wool or polyacrylnitrile, paper or wood.

It is well known that cationic compounds have a good affinity to negative charged hair or wool. These characteristics have been used to contact the hair with small molecules, but also with polymers.

Numerous cationic polymeric dyes have been disclosed for use as a colorant for keratin containing fibers, for example in U.S. Pat. No. 4,228,259; U.S. Pat. No. 4,182,612 or FR 2 456 764. These references teach that the polymer moiety has the cationic charge.

Improvement of hair dyes properties is already addressed in two new classes of hair dye technologies: polymeric dyes and disulfide dyes.

However, both technologies show limitations, especially washing fastness (polymeric dyes) and toxicological issues (disulfide dyes)

The present invention relates to a new technology for hair coloration. A disulfide moiety is covalently bound to a polymeric dye.

Surprisingly it was found that very good dyeing results are obtained with this new technology.

Therefore, the present invention relates to the reaction product of
(A) a polymeric backbone selected from the compounds of the formulas

   (A$_1$)

with
(B) a chromophore selected from the compounds of formulas

   (B$_1$)

   (B$_2$)

and

   (B$_3$)

wherein
T, U and Q independently from each other, represent repeating units of a polymer backbone;

$X_1$, $X_2$ and $X_3$ independently from each other are the direct bond; an optionally substituted, saturated or unsaturated, fused or non-fused aromatic or nonaromatic (heterocyclic) bivalent radical optionally comprising at least one heteroatom; a saturated or unsaturated, fused or non-fused aromatic or nonaromatic bivalent radical comprising at least one heteroatom, which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), hydroxy or halogen; or a bivalent radical of formula $$—(V)_t—(Z)_u—,$$  (B$_a$)

wherein
V is straight-chain or branched —$C_1$-$C_{12}$alkylene; —$C_2$-$C_{12}$alkenylene-; $C_5$-$C_{10}$cycloalkylene; $C_5$-$C_{10}$arylene; $C_5$-$C_{10}$arylene-($C_1$-$C_{10}$)alkylene-; —C(O)—; —(CH$_2$CH$_2$—O)$_{1-5}$—; —(CH$_2$CH$_2$CH$_2$—O)$_{1-5}$—; —C(O)O—; —OC(O)—; —N(R$_1$)—; —CON(R$_2$)—; —(R$_1$)NC(O)—; —O—; —S—; S(O)—; —S(O)—; S(O)$_2$—; —S(O)$_2$N(R$_1$)—; or —N$^+$(R$_1$)(R$_2$)—;
Z is a biradical of formula

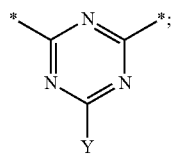   (B$_b$)

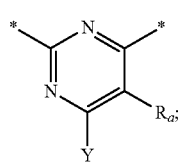   (B$_c$)

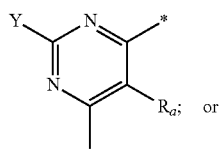   (B$_d$)

or

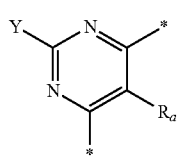   (B$_e$)

$R_1$ and $R_2$ independently from each other are hydrogen; $C_1$-$C_6$alkyl; $C_1$-$C_6$alkoxy; $C_1$-$C_6$-alkylamino; $C_6$-$C_{10}$aryloxy; or $C_6$-$C_{10}$arylamino;

$R_a$ is hydrogen; $C_1$-$C_6$alkyl; $C_1$-$C_6$-alkoxy; $C_1$-$C_6$-alkylamino; $C_6$-$C_{10}$aryloxy; $C_6$-$C_{10}$-arylamino; SO$_2$R$_5$; chlorine; or fluorine;

Y is $R_a$, $Y_1$, $Y_2$ or $Y_3$;

$Y_1$, $Y_2$ and $Y_3$ independently from each other are a residue of an organic dye;

G represents a functional group capable of reacting with the polymeric backbone (A) selected from halide, activated methoxy, hydroxy, tosylate, mesylate, carboxylic acid, carboxylic acid chloride, carboxylic ester, sulfonyl chloride, vinyl sulfone, acrylate, isocyanate, epoxide, anhydride, primary, secondary or tertiary amines and hydroxy;

m is a number from 0 to 50000;
n is a number from 0 to 50000; and
p is a number from 1 to 50000;
m and n independently from each other are 0, or 1;
wherein the sum of m+n+p≥3;
t and u independently from each other are 1, or 2;
and with (C) at least one sulfide containing compound of formula $$G\text{-}(Z_1)_r\text{—}X_3\text{—}S\text{—}Z_3\text{-}[\text{—}X_4\text{—}(Z_2)_q\text{-}G_1]_s, \quad (C_1)$$

or $$G\text{-}(Z_1)_r\text{—}X_5; \quad (C_2)$$

wherein $X_3$ and $X_4$ each independently from each other are unsubstituted or substituted, straight-chain or branched, interrupted or uninterrupted —$C_1$-$C_{10}$alkylene-; —$C_5$-$C_{10}$cycloalkylene-; $C_5$-$C_{10}$arylene; or —$C_5$-$C_{10}$arylene-($C_1$-$C_{10}$alkylene)-;

$X_5$ is a 5 to 7 membered heterocyclic ring containing a disulfide (S—S) bond $Z_1$ and $Z_2$ independently from each other are —C(O)—; —$C_2$-$C_{12}$alkenylene-; —(CH$_2$CH$_2$—O)$_{1-5}$—; —$C_1$-$C_{10}$alkylene($C_5$-$C_{10}$arylene)-; —$C_5$-$C_{10}$arylene-; —$C_5$-$C_{10}$cyclo-alkylene-; —C(O)O—; —OCO—; —N(R$_3$)—;

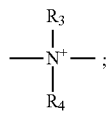

—CON(R$_4$)—; —(R$_5$)NC(O)—; —CH$_2$C(O)N(R$_6$)—; —(R$_6$)NC(O)CH$_2$—; —O—; —S—; —S(O)—; or —S(O)$_2$—;

$R_3$, $R_4$, $R_5$ and $R_6$ independently from each other are hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);

$G_1$ is hydrogen; or represents a functional group capable of reacting with the polymeric backbone (A) selected from halide, activated methoxy, hydroxy, tosylate, mesylate, carboxylic acid, carboxylic acid chloride, carboxylic ester, sulfonyl chloride, vinyl sulfone, acrylate, epoxide and anhydride;

q, r and s independently from each other are 0 or 1;

if s is 0, $Z_3$ is hydrogen; SR$_7$; or a group of formula

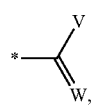

(C$_a$)

wherein $R_7$ is hydrogen; $C_1$-$C_{12}$alkyl; $C_6$-$C_{12}$aryl; or $C_6$-$C_{12}$aryl-$C_1$-$C_{12}$alkyl; or a radical of formula —(CH$_2$)$_v$—R$_8$;

$R_8$ is a radical of formula —NH—(CO)—R$_9$; —(CO)—R$_9$; —NR$_9$R$_{10}$; or OH;

$R_9$ and $R_{10}$ independently of each other are hydrogen; hydroxy; $C_1$-$C_5$alkyl; or $C_1$-$C_5$alkoxy; and v is a number from 1 to 4; and wherein the —(CH$_2$)$_v$— groups are optionally substituted by one or more than one —NR$_{11}$R$_{12}$ or —OR$_{12}$ groups, wherein $R_{11}$ or $R_{12}$ independently of another are hydrogen; or $C_1$-$C_5$alkyl;

V is hydrogen; $C_1$-$C_{12}$alkyl; $C_6$-$C_{12}$aryl; $C_6$-$C_{12}$aryl-$C_1$-$C_{12}$alkyl; —OR$_{13}$; —NR$_{13}$R$_{14}$, or —SR$_{13}$;

W is O; S; or N—R$_{15}$;

$R_{13}$, $R_{14}$ and $R_{15}$ independently from each other are hydrogen; $C_1$-$C_{12}$alkyl; $C_6$-$C_{12}$aryl; $C_6$-$C_{12}$aryl-$C_1$-$C_{12}$alkyl;

if s is 1, $Z_3$ is —S—;

wherein the polymeric backbone (A) can be reacted either first with the sulfide containing compound (C) and then with the chromophore (B); or first with the chromophore (B) and then with the sulfide containing compound (C); or the polymeric backbone (A) can be reacted simultaneously with the chromophore (B) and with the sulfide containing compound (C).

$C_1$-$C_{14}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecyl, dodecyl, tredecyl or tetradecyl.

$C_2$-$C_{14}$alkenyl is for example allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

$C_6$-$C_{10}$aryl is for example phenyl or naphthyl.

$C_1$-$C_{10}$alkylene is for example methylene, ethylene, propylene, isopropylene, n-butylene, sec-butylene, tert-butylene, n-pentylene, 2-pentylene 3-pentylene, 2,2'-dimethylpropylene, cyclopentylene, cyclohexylene, n-hexylene, n-octylene, 1,1',3,3'-tetramethylbutylene, 2-ethylhexylene, nonylene or decylene.

A biradical or radical of a heterocyclic compound is for example a biradical or radical of thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl.

Preferred biradical or radical of a heterocyclic compound is for example 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl.

More preferred cationic heterocyclic compounds are imidazolyl, pyridinyl, 1,3,4-triazolyl and 1,3-thiazolyl.

A biradical or radical of an aromatic compound is for example phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether or azobenzenyl.

The biradical or radical of a heterocyclic or aromatic compound is unsubstituted or mono- or poly-substituted, for example by $C_1$-$C_4$alkyl, $C_1$-$C_4$alkoxy, $C_1$-$C_4$alkylthio, halogen, e.g. fluorine, bromine or chlorine, nitro, trifluoromethyl, CN, SCN, $C_1$-$C_4$alkylsulfonyl, phenylsulfonyl, benzylsulfonyl, di-$C_1$-$C_4$alkylaminosulfonyl, $C_1$-$C_4$alkyl-carbonylamino, $C_1$-$C_4$alkoxysulfonyl or by di-(hydroxy-$C_1$-$C_4$alkyl)-aminosulfonyl.

"Anion" denotes, for example, an organic or inorganic anion, such as halide, preferably chloride and fluoride, sulfate, hydrogen sulfate, phosphate, boron tetrafluoride, carbonate, bicarbonate, oxalate or $C_1$-$C_8$alkyl sulfate, especially methyl sulfate or ethyl sulfate; anion also denotes lactate, formate, acetate, propionate or a complex anion, such as the zinc chloride double salt.

Preference is given to the reaction product of (A) a polymeric backbone selected from the compounds of the formulas $$*\!-\!\!\left[\!-\!T\!-\!\right]_n\!\!\left[\!-\!U\!-\!\right]_m\!\!\left[\!-\!Q\!-\!\right]_p\!\!-\!*$$ (A₁)

with (B) a chromophore selected from the compounds of formulas

G-X₁—Y₁; (B₁)

G-X₂—Y₂; (B₂)

and

G-X₃—Y₃ (B₃)

wherein

T, U and Q independently from each other, represent repeating units of a polymer backbone;

$X_1$, $X_2$ and $X_3$ independently from each other are the direct bond; an optionally substituted, saturated or unsaturated, fused or non-fused aromatic or nonaromatic (heterocyclic) bivalent radical optionally comprising at least one heteroatom; a saturated or unsaturated, fused or non-fused aromatic or nonaromatic bivalent radical comprising at least one heteroatom, which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), hydroxy or halogen; or a bivalent radical of formula —(V)$_t$(Z)$_u$—, (B$_a$)

wherein

V is straight-chain or branched —$C_1$-$C_{12}$alkylene; —$C_2$-$C_{12}$alkenylene-; $C_5$-$C_{10}$cycloalkylene; $C_5$-$C_{10}$arylene; $C_5$-$C_{10}$arylene-($C_1$-$C_{10}$)alkylene-; —C(O)—; —(CH₂CH₂—O)$_{1-5}$—; —(CH₂CH₂CH₂—O)$_{1-5}$—; —C(O)O—; —OC(O)—; —N($R_1$)—; —CON($R_2$)—; $R_1$)NC(O)—; —O—; —S—; —S(O)—; —S(O)₂—; —S(O)₂N($R_1$)—; or —N⁺($R_1$)($R_2$)—;

Z is a biradical of formula (B$_b$)

(B$_c$)

(B$_d$)

or (B$_e$)

$R_1$ and $R_2$ independently from each other are hydrogen; $C_1$-$C_6$alkyl; $C_1$-$C_6$alkoxy; $C_1$-$C_6$-alkylamino; $C_6$-$C_{10}$aryloxy; or $C_6$-$C_{10}$arylamino;

$R_a$ is hydrogen; $C_1$-$C_6$alkyl; $C_1$-$C_6$-alkoxy; $C_1$-$C_6$-alkylamino; $C_6$-$C_{10}$aryloxy; $C_6$-$C_{10}$-arylamino; SO₂$R_5$; chlorine; or fluorine;

Y is $R_a$, $Y_1$, $Y_2$ or $Y_3$;

$Y_1$, $Y_2$ and $Y_3$ independently from each other are a residue of an organic dye;

G represents a functional group capable of reacting with the polymeric backbone (A) selected from halide, activated methoxy, hydroxy, tosylate, mesylate, carboxylic acid, carboxylic acid chloride, carboxylic ester, sulfonyl chloride, vinyl sulfone, acrylate, isocyanate, epoxide, anhydride, primary, secondary or tertiary amines and hydroxy;

m is a number from 0 to 50000;

n is a number from 0 to 50000; and p is a number from 1 to 50000;

m and n independently from each other are 0, or 1;

wherein the sum of m+n+p≥3;

t and u independently from each other are 1, or 2;

and with (C) at least one sulfide containing compound of formula

G-(Z₁)$_r$—X₃—S—Z₃—[X₄—(Z₂)$_q$-G₁]$_s$, (C₁)

or

G-(Z₁)$_r$—X₅; (C₂)

wherein $X_3$ and $X_4$ each independently from each other are unsubstituted or substituted, straight-chain or branched, interrupted or uninterrupted —$C_1$-$C_{10}$alkylene-; —$C_5$-$C_{10}$cycloalkylene; $C_5$-$C_{10}$arylene; or —$C_5$-$C_{10}$arylene-($C_1$-$C_{10}$alkylene)-;

$X_5$ is a 5 to 7 membered heterocyclic ring containing a disulfide (S—S) bond $Z_1$ and $Z_2$ independently from each other are —C(O)—; —$C_2$-$C_{12}$alkenylene-; —(CH₂CH₂—O)$_{1-5}$—; —$C_1$-$C_{10}$alkylene($C_5$-$C_{10}$arylene)-; —$C_5$-$C_{10}$arylene-; —$C_5$-$C_{10}$cycloalkylene-; —C(O)O—; —OCO—; —N($R_3$)—;

$$-\!\!\begin{array}{c}R_3\\|\\N^+\!-\\|\\R_4\end{array}\!\!-;$$

—CON($R_4$)—; —($R_5$)NC(O)—; —CH₂C(O)N($R_6$)—; —($R_6$)NC(O)CH₂—; —O—; —S—; —S(O)—; or —S(O)₂—;

$R_3$, $R_4$, $R_5$ and $R_6$ independently from each other are hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);

$G_1$ is hydrogen; or represents a functional group capable of reacting with the polymeric backbone (A) selected from halide, activated methoxy, hydroxy, tosylate, mesylate, carboxylic acid, carboxylic acid chloride, carboxylic ester, sulfonyl chloride, vinyl sulfone, acrylate, epoxide and anhydride;

q, r and s independently from each other are 0 or 1;

if s is 0, $Z_3$ is hydrogen or a group of formula

wherein

V is hydrogen; $C_1$-$C_{12}$alkyl; $C_6$-$C_{12}$aryl; $C_6$-$C_{12}$aryl-$C_1$-$C_{12}$alkyl; —$OR_7$; —$NR_8R_9$, or —$SR_{10}$;

W is O; S; or N—$R_{11}$;

$R_7$, $R_8$, $R_9$, $R_{10}$ and $R_{11}$ independently from each other are hydrogen; $C_1$-$C_{12}$alkyl; $C_6$-$C_{12}$aryl; or $C_6$-$C_{12}$aryl-$C_1$-$C_{12}$alkyl;

if s is 1, $Z_3$ is —S—;

wherein the polymeric backbone (A) can be reacted either first with the sulfide containing compound (C) and then with the chromophore (B); or first with the chromophore (B) and then with the sulfide containing compound (C); or the polymeric backbone (A) can be reacted simultaneously with the chromophore (B) and with the sulfide containing compound (C).

In formulae ($B_1$) and ($B_2$) and ($B_3$) preferably $Y_1$, $Y_2$ and $Y_3$ are a residue of a cationically charged organic dye.

More preferably, $Y_1$, $Y_2$ and $Y_3$ independently from each other are selected from the group of anthraquinone, acridine, azo, disazo, azomethine, hydrazomethine, triphenylmethane, benzodifuranone, coumarine, diketopyrrolopyrrol, oxazine, dioxazine, diphenylmethane, formazane, indigoid indophenol, naphthalimide, naphthoquinone, nitroaryl, merocyanine, methine oxazine, perinone, perylene, pyrenequinone, phtalocyanine, phenazine, quinoneimine, quinacridone, quinophtalone, styryl, stilbene, xanthene, thiazine and thioxanthene dyes.

More preferably, $Y_1$, $Y_2$ and $Y_3$ independently from each other are selected from azo, azomethine, hydrazomethine, merocyanine, methine, oxazine and styryl dyes.

Most preferably $Y_1$, $Y_2$ and $Y_3$ have the same meaning.

Preferably in formula (A)

T, U and Q, independently from each other are selected from polyethylenimine, polypropyleneimine, polyvinylamine; polyvinylimine; polyetheramine; polysiloxane; polystyrene, polyvinylimidazol, polyvinylpyridine, DADMAC/DAA copolymers, polyetheramines, polyvinylalcohol, polyacrylate, polymethacrylate; polyureas, polyurethanes derived from hydroxyl-terminated polyethers, polyesters or polybutadienes on the one hand and aliphatic or aromatic polyisocyanates on the other, as well as precursors thereof; polyamides and copolyamides derived from diamines and dicarboxylic acids and/or from aminocarboxylic acids or the corresponding lactams; functionalized polysaccharide, starch, cellulose and lignin; and copolymers and blends of the mentioned polymers.

Especially preferred are polyethyleneimine, polyvinylamine, polyetheramines.

Polyethyleneimines can be prepared by known procedures as describes in Römpps Chemie Lexikon, 8. Aufl. 1992, S. 3532-3533 or in Ullmanns Enzyklopädie der Technischen Chemie, 4. Aufl. 1974, Bd. 8, S. 212-213. They have a molecular weight in the range of 200 bis 1 000 000 g/mol. Trade names are for example Lupasol® from BASF SE or Epomin from Nippon Shokubai.

Also preferred are polyamidoamines or polyvinylamines grafted with ethylenimine

Homopolymers and copolymers mentioned above may have any stereostructure including syndiotactic, isotactic, hemi-isotactic or atactic; where atactic polymers are preferred. Stereoblock polymers are also included.

Examples for copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof are for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

Examples for graft copolymers of vinyl aromatic monomers are styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

Examples for halogen-containing polymers are polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

Examples for polymers derived from α,β-unsaturated acids and derivatives thereof are polyacrylates and polymethacrylates; polymethyl methacrylates, polyacrylamides and polyacrylonitriles, impact-modified with butyl acrylate.

Examples for copolymers of the monomers mentioned above with each other or with other unsaturated monomers are acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

Examples for polymers derived from unsaturated alcohols and amines or the acyl derivatives or acetals thereof are for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in above.

Examples for homopolymers and copolymers of cyclic ethers are polyalkylene glycols, polyethylene oxide, polypropylene oxide or copolymers thereof with bisglycidyl ethers.

Examples for polyacetals are polyoxymethylene and those polyoxymethylenes which contain ethylene oxide as a comonomer; polyacetals modified with thermoplastic polyurethanes, acrylates or MBS.

Examples for polyamides and copolyamides derived from diamines and dicarboxylic acids and/or from aminocarboxylic acids or the corresponding lactams are polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

Examples for natural polymers are cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

Preferably both the polymer backbone (T, U and Q) and residue of an organic dye ($Y_1$ and $Y_2$) have a functional group selected from the electrophilic group selected from halide, tosylate, mesylate, methoxy, acid chloride, sulfonyl chloride, epoxides, anhydride; or a nucleophilic group selected from amine, hydroxyl and thiol.

Preferably the molecular weight of the polymeric dye is from 400 to $2*10^6$, most preferably 1000 to 500000.

"Anion" denotes, for example, an organic or inorganic anion, such as halide, preferably chloride and fluoride, sulfate, hydrogen sulfate, phosphate, boron tetrafluoride, carbonate, bicarbonate, oxalate or $C_1$-$C_8$alkyl sulfate, especially methyl sulfate or ethyl sulfate; anion also denotes lactate, formate, acetate, propionate or a complex anion, such as the zinc chloride double salt.

Most preferably are reaction products wherein the sulfide containing compound (C) corresponds to formula

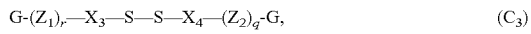
(C_3)

wherein
$Z_1$, $Z_2$, $X_3$, $X_4$, G, q and r are defined as in formula (C$_1$).

Also preferred are reaction products wherein the sulfide containing compound (C) corresponds to formula

(C_4)

or

(C_5)

wherein
$R_{12}$ is hydrogen; $C_1$-$C_{12}$alkyl; or phenyl-$C_1$-$C_4$alkyl; and
$Z_3$ is hydrogen; or a thio ester group of formula (C$_a$) as defined in formula (C$_1$); and
$Z_1$, $X_3$, G and r are defined as in formula (C$_1$).

Most preferred are reaction products wherein the sulfide containing compound (C) corresponds to formula

(C_6)

wherein
$Z_1$, G and r are defined as in formula (C$_2$).

Most preferred are reaction products which correspond to the reaction product of formula

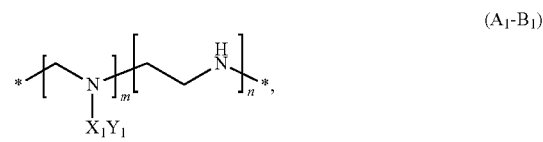
(A_1-B_1)

with the sulfide containing compound

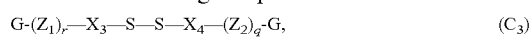
(C_3)

wherein
X1 as described in Formula B1
$Y_1$ is a residue of an organic dye selected from azo, disazo, azomethine, hydrazomethine, merocyanine, methine, oxazine and styryl dyes;
m and n are a number from 0 to 1000; wherein the sum of m and n≥3; and
$Z_1$, $Z_2$, $X_3$, $X_4$, G, q and r are defined as in formula (C$_1$).

Further preferred are reaction products which correspond to the reaction product of formula

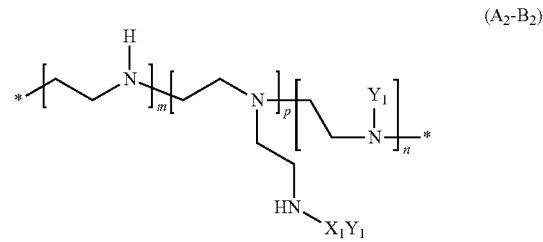
(A_2-B_2)

with the sulfide containing compound

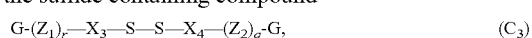
(C_3)

wherein
$X_1$ is as defined as in Formula B1
$Y_1$ is a residue of an organic dye selected from azo, disazo, azomethine, hydrazomethine, merocyanine, methine, oxazine and styryl dyes;
m, n and p are a number from 0 to 1000; wherein the sum of m, n and p≥3; and
$Z_1$, $Z_2$, $X_3$, $X_4$, G, q and r are defined as in formula (C$_1$).

A further embodiment of the present invention relates to processes for the preparation of the reaction products according to the invention.

Generally, the process comprises stepwise or simultaneous reaction of the polymeric backbone (A), the chromophore (B) or the chromophore building blocks B' and B" and the sulfide containing compound (C) to a final product ABC, as shown in the following reaction sequences:
a) A+B->AB (step 1)
   AB+C->ABC (step 2) or
b) A+C->AC (step 1)
   AC+B->ABC (step 2) or
c) A+B+C->ABC.

Preferably the intermediates AB and AC can be reacted to the final products without being isolated. It may also be advantageous to isolate the intermediates AB and AC before they are reacted to the final products.

In the reaction sequences a), b), c) preferably (A) possesses nucleophilic functionalities and B and C posses at least one electrophilic functionality.

Alternatively (A) possesses electrophilic functionalities and (B) and (C) posses at least one nucleophilic functionality.

The nucleophilic functionalities can be selected from acetate, azlactones, brosylate, mesylate, nosylate, tosylate, trifluoracetate, trifluorsulfonate, chloro, bromine or iodine, sulfate esters, vinylsulfones, carboxylic acids, their esters or acid chlorides, epoxides or halohydrine ethers.

The synthetic methods for the preparation of the chromophores (B) are described for example in Ullmann's Encyclopedia of Industrial Chemistry.

In general the central step in the preparation of B is the reaction of two building blocks B' and B":
d) B'+B"->B It may be advantageous to include in the preparation of B a quaternisation step using an alkylating agent, e.g. dimethylsulfate, methyl iodide, methyl chloride, methyl bromide or the higher carbon homologues of these reagents.

For the preparation of the reaction products ABC it may be advantageous that building block B' first react with the polymeric backbone (A) and then with B":
e) A+B'->AB' (step 1)
   AB'+B"->AB (step 2)
   AB+C->ABC (step 3) or
f) A+C->AC (step 1)
   AC+B'->AB'C (step 2)
   AB'C+B"->ABC (step 3)

The reactions are generally initiated by contacting; for example by mixing together the starting compounds or by dropwise addition of one starting compound to the other.

Customary, the temperature is in the range from 273 to 423 K, preferably in the range from 290 to 300 K during the mixing of the starting compounds.

The reaction time is generally dependent on the reactivity of the starting compounds, on the reaction temperature chosen and on the desired conversion. The chosen duration of reaction is usually in the range from one hour to three days.

The reaction temperature for the reaction of the compounds is advisable to be selected in the range from 273 to 423K, especially in the range from 273 to 335K.

The reaction pressure is generally in the range from 70 kPa to 10 MPa, especially from 90 kPa to 5 MPa, and is more especially atmospheric pressure.

It may be desirable to conduct the reaction of compounds in the presence of a catalyst.

The molar ratio of compound A, B, B', B" or C to the catalyst is generally selected in the range from 10:1 to 1:5, especially in the range from 10:1 to 1:1.

Suitable catalysts are for example an alkali metal $C_1$-$C_6$alkyloxide, such as sodium-, potassium or lithium $C_1$-$C_6$alkyloxide, preferably sodium methoxide, potassium methoxide or lithium methoxide, or sodium ethoxide, potassium ethoxide or lithium ethoxide; or tertiary amines, for example, such as chinuclidine, N-methylpiperidine, pyridine, trimethylamine, triethylamine, trioctylamine, 1,4-diazabicyclo[2.2.2]octan, chinuclidine, N-methylpiperidine; or alkali metal acetate, for example such as sodium acetate, potassium acetate, or lithium acetate.

Preferred are potassium acetate, sodium methoxide, pyridine and 1,4-diazabicyclo[2.2.2]octane.

In addition, the reactions may be carried out with or without a solvent, but are preferably carried out in the presence of a solvent.

Solvents are organic solvents and water, or a mixture of organic solvents or a mixture of organic solvents and water.

Organic solvents are for example, protic or aprotic polar organic solvents, such as alcohols, for example methanol, ethanol, n-propanol, isopropanol, butanol or glycols, especially isopropanol, or nitrile, such as acetonitrile or propionitrile, or amide, such as dimethylformamide, dimethylacetamide or N-methylpyridine, N-methylpyrolidon, or sulfoxide, such as dimethylsulfoxide, or mixtures thereof.

The product prepared according to the process of the present invention may be advantageously worked up and isolated, and if desired be purified.

Customary, the work up starts by decreasing the temperature of the reaction mixture in the range from 280 to 300 K, especially in the range from 290 to 300 K.

It may be of advantageous to decrease the temperature slowly, over a period of several hours.

For the isolation it may also be advantageous to add organic or inorganic acids, like hydrochloric acid, methanesulfonic acid, acetic acid or formic acid to the reaction mixture.

In general, the reaction product is usually filtered and then washed with water or a salt solution and subsequently dried.

Filtration is normally carried out in standard filtering equipment, for example Büchner funnels, filter presses, pressurized suction filters, preferably in vacuo.

The temperature for the drying is dependent on the pressure applied. Drying is usually carried out in vacuo at 50-200 mbar.

The drying is usually carried out at a temperature in the range from 313 to 363 K, especially from 323 to 353 K, and more especially in the range from 328 to 348 K.

Advantageously the product is purified by recrystallization after isolation.

Organic solvents and solvent mixtures are suitable for the recrystallization, preferably alcohols, for example methanol, ethanol, 2-propanol or butanol, especially 2-propanol.

The reaction products according to the invention are suitable for dyeing organic materials, such as keratin-containing fibers, wool, leather, silk, cellulose or polyamides, cotton or nylon, and preferably human hair. The dyeings obtained are distinguished by their depth of shade and their good fastness properties to washing, such as, for example, fastness to light, shampooing and rubbing.

The reaction products according to the invention are used, in particular, as dyes for dyeing and printing textile materials, paper and leather and for the preparation of inks. Suitable textile materials are natural and synthetic materials which can be dyed by cationic processes. The reaction products according to the invention are preferably employed for dyeing and printing paper, thin cardboard and cardboard in the pulp and on the surface, and also textile materials which, for example, advantageously consist of homopolymers or copolymers of acrylonitrile or of synthetic polyamides or polyesters modified with acid groups. These textile materials are preferably dyed in an aqueous, neutral or acid medium by the exhaust method, if appropriate under pressure, or by the continuous method. In this regard, the textile material can be in a very wide variety of different forms, for example as fibres, filaments, woven fabrics, knitted fabrics, piece goods and made-up articles, such as shirts or pullovers.

The dyes according to the invention make it possible to produce level dyeings or prints which are distinguished by very good overall fastness properties, in particular a very high degree of exhaustion and good fastness properties to water.

Furthermore, the reaction products according to the invention can also be used for dyeing and printing natural and regenerated cellulose materials, in particular cotton and viscose, deeply coloured dyeings also being obtained.

On these textile materials, the reaction products according to the invention have a good substantially a good degree of exhaustion, and the dyeings obtained exhibit very good fastness properties, in particular fastness to wet processing.

A preferred use of the reaction products according to the invention is their use for dyeing paper of all kinds, in particular bleached, unsized and sized, lignin-free paper, it being possible to use bleached or unbleached pulp as the starting material and to use hardwood pulp or softwood pulp, such as birch and/or pine sulfite and/or sulfate pulp. These compounds are very particularly suitable for dyeing unsized paper (for example table napkins, table cloths and hygiene papers) as a result of their very high affinity for this substrate.

The reaction products according to the invention are very strongly absorbed onto these substrates, the effluents remaining virtually colourless.

The dyeings obtained are distinguished by good overall fastness properties, such as good fastness to light, and at the same time have a high clarity and depth of colour and fastness to wet processing, i.e. they exhibit no tendency to bleeding when dyed paper is brought into contact under wet conditions with moist white paper. In addition they exhibit good fastness to alum, acids and alkalis. The fastness to wet processing relates not only to water, but also to milk, fruit juices and sweetened mineral water; owing to their good fastness to alcohol, the dyes are also fast to alcoholic beverages. This property is particularly desirable, for example, for table napkins and table cloths in the case of which it can be expected that the dyed paper will come into contact in a wet state (for example impregnated with water, alcohol, surfactant solution etc.) with outer surfaces, such as textiles, paper and the like, which must be protected against soiling.

The high affinity for paper and the high exhaustion rate of the novel dyestuffs is of great advantage for the continuous dyeing of paper.

Generally, hair dyeing agents on a synthetic base may be classified into three groups:
  temporary dyeing agents
  semipermanent dyeing agents, and
  permanent dyeing agents.

The multiplicity of shades of the dyes can be increased by combination with other dyes.

Therefore the reaction products of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Especially preferred is the combination of the reaction products of the present invention with other polymeric dyes as described in GB 2440219, WO 09/090,121, WO 09/090,122, WO 09/090,124 or WO 09/090,125.

Direct dyes are of natural origin or may be prepared synthetically. They are uncharged, cationic or anionic, such as acid dyes.

The reaction products may be used in combination with at least one single direct dye.

Direct dyes do not require any addition of an oxidizing agent to develop their dyeing effect. Accordingly the dyeing results are less permanent than those obtained with permanent dyeing compositions. Direct dyes are therefore preferably used for semipermanent hair dyeings.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie-und Handelsunternehmen für Arzneimittel, Reformwaren und Körperpflegemittel e.V., Mannheim.

Furthermore, the reaction products according to the present invention may be combined with at least one cationic azo dye, for example the compounds disclosed in GB-A-2 319 776 as well as the oxazine dyes described in DE-A-299 12 327 and mixtures thereof with the other direct dyes mentioned therein, and even more preferred with cationic dyes such as Basic Yellow 87, Basic Orange 31 or Basic Red 51, or with cationic dyes as described in WO 01/66646, especially example 4, or with cationic dyes as described in WO 02/31056, especially example 6, the compound of formula 106; or the cationic dye of formula (3) as described in EP-A-714,954.

The reaction products according to the present invention may also be combined with acid dyes, for example the dyes which are known from the international names (Color index), or trade names.

The reaction products according to the present invention may also be combined with uncharged dyes.

Furthermore, the reaction products according to the present invention may also be used in combination with oxidation dye systems.

Oxidation dyes, which, in the initial state, are not dyes but dye precursors are classified according to their chemical properties into developer and coupler compounds.

Suitable oxidation dyes are described for example in
  DE 19 959 479, especially in col 2, l. 6 to col 3, l. 11;
  "Dermatology", edited by Ch. Culnan, H. Maibach, Verlag Marcel Dekker Inc., New York, Basle, 1986, Vol. 7, Ch. Zviak, The Science of Hair Care, chapter 8, on p. 264-267 (oxidation dyes);

Preferred developer compounds are for example primary aromatic amines, which are substituted in the para- or ortho-position with a substituted or unsubstituted hydroxy- or amino residue, or diaminopyridine derivatives, heterocyclic hydrazones, 4-aminopyrazol derivatives, 2,4,5,6-tetraminopyrimidine derivatives, or unsaturated aldehydes as described in DE 19 717 224, especially on p. 2, l. 50 to l. 66 and on p. 3 l. 8 to l. 12, or cationic developer compounds as described in WO 00/43367, especially on p., 2 l. 27 to p. 8, l. 24, in particular on p. 9, l. 22 to p. 11, l. 6.

Furthermore, developer compounds in their physiological compatible acid addition salt form, such as hydrochloride or sulfate can be used. Developer compounds, which have aromatic OH radicals are also suitable in their salt form together with a base, such as alkali metalphenolates.

Preferred developer compounds are disclosed in DE 19959479, p. 2, l. 8-29.

More preferred developer compounds are p-phenylendiamine, p-toluoylendiamine, p-, m- o-aminophenol, N,N-bis-(2-hydroxyethyl)-p-phenylenediamine sulfate, 2-amino-4-hydroxyethylaminoanisole sulfate, hydroxyethyl-3,4-methylenedioxyanil., 1-(2'-hydroxyethyl)-2,5-diaminobenzene, 2,6-dimethoxy-3,5-diamino-pyridine, hydroxypropyl-bis-(N-hydroxyethyl-p-phenylenediamine) hydrochloride, hydroxyethyl-p-phenylenediamine sulfate, 4-amino-3-methylphenol, 4-methylaminophenol sulfate, 2-aminomethyl-4-aminophenol, 4,5-diamino-1-(2-hydroxyethyl)-1H-pyrazol, 4-amino-m-cresol, 6-amino-m-cresol, 5-amino-6-chloro-cresol, 2,4,5,6-tetraminopyrimidine, 2-hydroxy-4,5,6-triaminopyrimidine or 4-hydroxy-2,5,6-triaminopyrimidine sulfate.

Preferred coupler compounds are m-phenylendiamine derivatives, naphthole, resorcine and resorcine derivatives, pyrazolone and m-aminophenol derivatives, and most preferably the coupler compounds disclosed in DE 19959479, p. 1, l. 33 to p. 3, l. 11.

The reaction products according to the present invention may also be used together with unsaturated aldehydes as disclosed in DE 19 717 224 (p. 2, l. 50 to l. 66 and on p. 3 l. 8 to l. 12) which may be used as direct dyes or, alternatively together with oxidation dye precursors.

Further preferred for a combination with a reaction products according to the present invention are the following oxidation dye precursors:
  the developer/-coupler combination 2,4,5,6-tetraminopyrimidine and 2-methylresorcine for assessing of red shades;
  p-toluenediamine and 4-amino-2-hydroxytoluene for assessing of blue-violet shades;
  p-toluenediamine and 2-amino-4-hydroxyethylaminoanisole for assessing of blue shades;
  p-toluenediamine and 2,4-diamino-phenoxyethynol for assessing of blue shades;
  methyl-4-aminophenol and 4-amino-2-hydroxytoluene for assessing of orange shades;
  p-toluenediamine and resorcine for assessing of brown-green shades;
  p-toluenediamine and 1-naphthol for assessing of blue-violet shades, or
  p-toluenediamine and 2-methylresorcine for assessing of brown-gold shades.

Furthermore, autooxidizable compounds may be used in combination with the reaction products according to the present invention.

The reaction products according to the present invention may also be used in combination with naturally occurring dyes.

Furthermore, the reaction products according to the present invention may also be used in combination with capped diazotized compounds.

Suitable diazotized compounds are for example the compounds of formulae (1)-(4) in WO 2004/019897 (bridging gages 1 and 2) and the corresponding water soluble coupling components (I)-(IV) as disclosed in the same reference on p. 3 to 5.

The present invention also relates to formulations, which are used for the dyeing of organic materials, preferably keratin-containing fibers, and most preferably human hair, comprising at least one reaction product according to the present invention.

Preferably the reaction products according to the present invention are incorporated into the composition for treating organic material, preferably for dyeing in amounts of 0.001-5% by weight (hereinafter indicated merely by "%"), particularly 0.005-4%, more particularly 0.2-3%, based on the total weight of the composition.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, l. 16 to 31.

The pH value of the ready-to-use dyeing compositions is usually from 2 to 11, preferably from 5 to 10.

The dyeing compositions of the present invention are applied on the hair in a temperature range of 5 to 200, preferably 18 to 80, and most preferably from 20 to 40° C.

One preferred embodiment of the present invention relates to the formulation of dyes, wherein reaction products according to the present invention are in powder form.

Powder formulations are preferably used if stability and/or solubility problems as for example described in DE 197 13 698, p. 2, l. 26 to 54 and p. 3, l. 51 to p. 4, l. 25, and p. 4, l. 41 to p. 5 l. 59.

Suitable cosmetic hair-care formulations are hair-treatment preparations, e.g. hair-washing preparations in the form of shampoos and conditioners, hair-care preparations, e.g. pretreatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, l. 70 to col 3, l. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts; for example emulsifiers may be present in the dyeing compositions in concentrations from 0.5 to 30% by weight and thickeners in concentrations from 0.1 to 25% by weight of the total dyeing composition.

Further carriers for dyeing compositions are for example described in "Dermatology", edited by Ch. Culnan, H. Maibach, Verlag Marcel Dekker Inc., New York, Basle, 1986, Vol.

7, Ch. Zviak, The Science of Hair Care, chapter 7, p. 248-250, especially on p. 243, I. 1 to p. 244, I. 12.

If the reaction products according to the present invention are used together with oxidation dyes and/or the addition salts thereof with an acid, they may be stored separately or together. Preferably the oxidation dyes and the direct dyes which are not stable to reduction are stored separately.

The reaction products according to the present invention may be stored in a liquid to pastelike preparation (aqueous or non-aqueous) or in the form of a dry powder.

When the dyes are stored separately, the reactive components are intimately mixed with one another directly before use. In the case of dry storage, a defined amount of hot (from 50 to 80° C.) water is usually added and a homogeneous mixture prepared before use.

The dyeing compositions according to the invention may comprise any active ingredients, additives or adjuvants known for such preparations, like surfactants, solvents, bases, acids, perfumes, polymeric adjuvants, thickeners and light stabilizers.

The following adjuvant are preferably used in the hair dyeing compositions of the present invention:-non-ionic polymers-cationic polymers, acrylamide/dimethyldiallylammonium chloride copolymers, diethyl-sulfate-quaternised dimethylaminoethyl methacrylate/vinylpyrrolidone copolymers, vinylpyrrolidone/imidazolinium methochloride copolymers; quarternised polyvinyl alcohol, zwitterionic and amphoteric polymers, anionic polymers, thickeners, structuring agents, hair-conditioning compounds, protein hydrolysates, perfume oils, dimethyl isosobitol and cyclodextrins, solubilizers, anti-dandruff active ingredients, substances for adjusting the pH value, panthenol, pantothenic acid, allantoin, pyrrolidonecarboxylic acids and salts thereof, plant extracts and vitamins, cholesterol; -light stabilizers and UV absorbers, consistency regulators, fats and waxes, fatty alkanolamides, polyethylene glycols and polypropylene glycols having a molecular weight of from 150 to 50 000, complexing agents, swelling and penetration substances, opacifiers, pearlising agents, propellants, antioxidants, sugar-containing polymers, quaternary ammonium salts and bacteria inhibiting agents.

Suitable surfactants are zwitterionic or ampholytic, or more preferably anionic, non-ionic and/or cationic surfactants.

Suitable anionic surfactants in the dyeing compositions according to the present invention include all anionic surface-active substances that are suitable for use on the human body. Such substances are characterized by an anionic group that imparts water solubility, for example a carboxylate, sulfate, sulfonate or phosphate group, and a lipophilic alkyl group having approximately 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanol ammonium salts having 2 or 3 carbon atoms in the alkanol group:

- linear fatty acids having 10 to 22 carbon atoms (soaps),
- ether carboxylic acids of formula R—O—($CH_2$—$CH_2$—O)$_x$—$CH_2$—COOH, in which R is a linear alkyl group having 10 to 22 carbon atoms and x=0 or from 1 to 16,
- acyl sarcosides having 10 to 18 carbon atoms in the acyl group,
- acyl taurides having 10 to 18 carbon atoms in the acyl group,
- acyl isothionates having 10 to 18 carbon atoms in the acyl group,
- sulfosuccinic mono- and di-alkyl esters having 8 to 18 carbon atoms in the alkyl group and sulfosuccinic monoalkylpolyoxyethyl esters having 8 to 18 carbon atoms in the alkyl group and from 1 to 6 oxyethyl groups,
- linear alkane sulfonates having 12 to 18 carbon atoms,
- linear α-olefin sulfonates having 12 to 18 carbon atoms,
- α-sulfo fatty acid methyl esters of fatty acids having 12 to 18 carbon atoms,
- alkyl sulfates and alkyl polyglycol ether sulfates of formula R'—O($CH_2$—$CH_2$—O)$_{x'}$—$SO_3H$, in which R' is a preferably linearar alkyl group having 10 to 18 carbon atoms and x'=0 or from 1 to 12,
- mixtures of surface-active hydroxysulfonates according to DE-A-3 725 030;
- sulfated hydroxyalkylpolyethylene and/or hydroxyalkylenepropylene glycol ethers according to DE-A-3 723 354, especially p. 4, I. 42 to 62,
- sulfonates of unsaturated fatty acids having 12 to 24 carbon atoms and 1 to 6 double bonds according to DE-A-3 926 344, especially p. 2, I. 36 to 54,
- esters of tartaric acid and citric acid with alcohols which are addition products of approximately from 2 to 15 molecules of ethylene oxide and/or propylene oxide with fatty alcohols having from 8 to 22 carbon atoms, or
- anionic surfactants, as described in WO 00/10518, especially p. 45, I. 11 to p. 48, I. 3.

Preferred anionic surfactants are alkyl sulfates, alkyl polyglycol ether sulfates and ether carboxylic acids having 10 to 18 carbon atoms in the alkyl group and up to 12 glycol ether groups in the molecule, and also especially salts of saturated and especially unsaturated $C_8$-$C_{22}$-carboxylic acids, such as oleic acid, stearic acid, isostearic acid and palmitic acid.

Surface-active compounds that carry at least one quaternary ammonium group and at least one —COO⁻ or —$SO_3^-$ group in the molecule are terminated zwitterionic surfactants. Preference is given the so-called betaines, such as the N-alkylN,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazoline having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocoamidopropyl betaine.

Ampholytic surfactants are surface-active compounds that, in addition to a $C_8$-$C_{18}$-alkyl or -acyl group and contain at least one free amino group and at least one —COOH or —$SO_3H$ group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$-$C_{18}$acylsarcosine.

Suitable non-ionic surfactants are described in WO 00/10519, especially p. 45, I. 11 to p. 50, I. 12. Non-ionic surfactants contain as hydrophilic group, for example, a polyol group, a polyalkylene glycol ether group or a combination of polyol and polyglycol ether groups. Such compounds are, for example:

- addition products of 2 to 30 mol of ethylene oxide and/or 0 to 5 mol of propylene oxide with linear fatty alcohols having 8 to 22 carbon atoms, with fatty acids having 12 to 22 carbon atoms and with alkylphenols having 8 to 15 carbon atoms in the alkyl group, $C_{12}$-$C_{22}$ fatty acid mono- and di-esters of addition products of 1 to 30 mol of ethylene oxide with glycerol, $C_8$-$C_{22}$alkyl-mono- and -oligo-glycosides and ethoxylated analogues thereof, addition products of 5 to 60 mol of ethylene oxide with castor oil and hydrogenated castor oil, addition products of ethylene oxide with sorbitan fatty acid esters, addition products of ethylene oxide with fatty acid alkanolamides.

The surfactants which are addition products of ethylene and/or propylene oxide with fatty alcohols or derivatives of such addition products may either be products having a "normal" homologue distribution or products having a restricted homologue distribution. "Normal" homologue distribution are mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts.

The use of products having restricted homologue distribution may be preferred.

Examples of cationic surfactants that can be used in the dyeing compositions according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyldimethyl-lammonium chloride, lauryldimethylammonium chloride, lauryldimethylbenzylammonium chloride and tricetylmethyl-ammonium chloride. Further cationic surfactants that can be used in accordance with the invention are quaternised protein hydrolysates.

Also suitable are cationic silicone oils, such as, for example, the commercially available products Q2-7224 (manufacturer: Dow Corning; a stabilised trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quaternium-80), or silicones, as described in WO 00/12057, especially p. 45, l. 9 to p. 55, l. 2.

Alkylamidoamines, especially fatty acid amidoamines, such as the stearylamidopropyldimethylamine obtainable under the name Tego Amid® 18 are also preferred as surfactants in the present dyeing compositions. They are distinguished not only by a good conditioning action but also especially by their good biodegradability.

Quaternary ester compounds, so-called "esterquats", such as the methyl hydroxyalkyldialkoyloxyalkylammonium methosulfates marketed under the trademark Stepantex®, are also very readily biodegradable.

An example of a quaternary sugar derivative that can be used as cationic surfactant is the commercial product Glucquat®100, according to CTFA nomenclature a "lauryl methyl gluceth-10 hydroxypropyl dimonium chloride".

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

The reaction products according to the present invention are suitable for the dyeing of organic material, preferably keratin-containing fibres.

A further preferred embodiment of the present invention relates to a method of treating keratin-containing fibers with a reaction product according to the present invention.

The process comprises
(a) contacting the keratin fiber with at least one compound of the reaction product according to the present invention
(b) leaving the fibers to stand, and
(c) then rinsing the fiber.

The process for dyeing is for example described in WO 01/66646 on page 15, line 32 to page 16, line 2.

A further preferred method comprises treating the hair in the presence of a reduction agent.

Preferred reduction agents are for example thioglycol acid or salts thereof, glycerin monothioglycolat, cystein, 2-mercaptopropionic acid, 2-mercaptoethylamine, thiolactic acid, thioglycerine, sodium sulfite, dithionithe, ammonium sulfite, sodium bisulfite, sodium metabisulfite, hydroquinone, phosphines, borohydride, cyanoborohydride, triacetoxy borohydride, trimethoxy borohydride salts (sodium, lithium, potassium, calcium quaternary salts).

Furthermore, the present invention relates to a process, comprising treating the hair with
(a) optionally a reduction agent,
(b) the reaction product according to the present invention, and
(c) optionally with an oxidizing agent.

The step (a) may be of short duration from 0.1 sec to 30 minutes, for example from 0.1 seconds to 10 minutes with a reducing agent mentioned above.

Preferably, the process comprises the steps of
a) dyeing the keratin-containing fiber with at least one of the reaction product according to the present invention,
b) wearing the colored hair for the desired period of time, and
c) removing the color applied in step a) from hair by contacting the hair with an aqueous based color removal composition containing a reducing agent capable of disrupting the —S—S-bonds between the dye molecule and the hair fiber surface to cause the dye molecule to become disassociated from the fiber.

The application of the dyes on the hair may be carried out at temperatures ranging from 15° to 100° C. Generally the application is carried out at room temperature.

The sequence of the reaction steps is generally not important; the reduction agent can be applied first or in a final step.

Usually, the oxidizing agent is applied together with an acid or a base.

The acid is for example citric acid, phosphoric acid or tartrate acid.

The base is for example sodium hydroxide, ammonia or monoethanolamine.

The reaction products according to the present invention are suitable for all-over dyeing of the hair, that is to say when dyeing the hair on a first occasion, and also for re-dyeing subsequently, or dyeing of locks or parts of the hair.

The reaction products according to the present invention are applied on the hair for example by massage with the hand, a comb, a brush, or a bottle, or a bottle, which is combined with a comb or a nozzle.

Further preferred is a process for dyeing keratin-containing fibers which comprises treating the keratin-containing fiber with at least one reaction product according to the present invention, a base and an oxidizing agent.

The oxidation dyeing process usually involves lightening, that is to say that it involves applying to the keratin-containing fibers, at basic pH, a mixture of bases and aqueous hydrogen peroxide solution, leaving the applied mixture to stand on the hair and then rinsing the hair. It allows, particularly in the case of hair dyeing, the melanin to be lightened and the hair to be dyed.

Lightening the melanin has the advantageous effect of creating a unified dyeing in the case of grey hair, and, in the case of naturally pigmented hair, of bringing out the color, that is to say of making it more visible.

In general, the oxidizing agent containing composition is left on the fiber for 0.1 to 15 minutes, in particular for 0.1 to 5 minutes at 15 to 45° C., usually in amounts of 30 to 200 g.

Oxidizing agents are for example persulfate or diluted hydrogen peroxide solutions, hydrogen peroxide emulsions or hydrogen peroxide gels, alkaline earth metal peroxides, organic peroxides, such as urea peroxides, melamine peroxides. Alkalimetalbromate fixations or enzymes are also appropriate if a shading powder on the basis of semi-permanent, direct hair dyes is used.

Further preferred oxidizing agents are
oxidizing agents to achieve lightened coloration, as described in WO 97/20545, especially p. 9, l. 5 to 9,
oxidizing agents in the form of permanent-wave fixing solution, as described in DE-A-19 713 698, especially p. 4, l. 52 to 55, and l. 60 and 61 or EP-A-1062940, especially p. 6, l. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% b.w. the corresponding composition.

The oxidizing agents may be present in the dyeing compositions according to the invention preferably in an amount from 0.01% to 6%, especially from 0.01% to 1%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

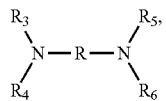

wherein
R is a propylene residue, which may be substituted with OH or $C_1$-$C_4$alkyl,
$R_3$, $R_4$, $R_5$ and $R_6$ are independently or dependently from each other hydrogen, $C_1$-$C_4$alkyl or hydroxy-($C_1$-$C_4$)alkyl.

The pH-value of the oxidizing agent containing composition is usually about 2 to 7, and in particular about 2 to 5.

One preferred method of applying formulations comprising the reaction products according to the present invention on the keratin-containing fiber, preferably the hair is by using a multi-compartment dyeing device or "kit" or any other multi-compartment packaging system, as described for example in WO 97/20545 on p. 4, l. 19 to l. 27.

The first compartment contains for example at least one reaction product according to the present invention and optionally further direct dyes and a basifying agent, and in the second compartment an oxidizing agent; or in the first compartment at least one reaction product according to the present invention and optionally further direct dyes, in the second compartment a basifying agent and in the third compartment an oxidizing agent.

A further preferred embodiment of the present invention relates to a method of dyeing hair with oxidative dyes, which comprises
(a) mixing at least one reaction product according to the present invention and optionally at least one coupler compound and at least one developer compound, and an oxidizing agent, which optionally contains at least one further dye, and
(b) contacting the keratin-containing fibers with the mixture as prepared in step (a).

The pH-value of the oxidizing agent free composition is usually from 3 to 11, and in particular from 5 to 10, and most particular about 9 to 10.

Preferably, a ready-to-use composition is prepared according to a first preferred embodiment by a process which comprises a preliminary step which involves separately storing, on the one hand, a composition (A) comprising, in a medium which is suitable for dyeing, at least one developer compound, especially selected from para-phenylenediamines and bis(phenyl)alkylenediamines, and the acid-addition salts thereof, at least one coupler, especially selected from meta-phenylenediamines and the acid-addition salts thereof, and at least one reaction product according to the present invention, on the other hand, a composition (B) containing, in a medium which is suitable for dyeing, at least one oxidizing agent and mixing (A) and (B) together immediately before applying this mixture to the keratin-containing fibers.

According to a second preferred embodiment for the preparation of the ready-to-use dye composition, the process includes a preliminary step which involves separately storing, on the one hand, a composition (A) comprising, in a medium which is suitable for dyeing, at least one developer compound, especially selected from para-phenylenediamines and bis(phenyl)alkylenediamines, and the acid-addition salts thereof, at least one coupler compound, especially selected from meta-phenylenediamines and the acid-addition salts thereof; on the other hand, a composition (A') comprising, in a medium which is suitable for dyeing, at least one reaction product according to the present invention, and, finally, a composition (B) containing, in a medium which is suitable for dyeing, at least one oxidizing agent as defined above, and mixing them together at the time of use immediately before applying this mixture to the keratin-containing fibers.

The composition (A') used according to this second embodiment may optionally be in powder form, the dye(s) of formula (1) (themselves) constituting, in this case, all of the composition (A') or optionally being dispersed in an organic and/or inorganic pulverulent excipient.

When present in the composition A', the organic excipient may be of synthetic or natural origin and is selected in particular from crosslinked and non-crosslinked synthetic polymers, polysaccharides such as celluloses and modified or unmodified starches, as well as natural products such as sawdust and plant gums (guar gum, carob gum, xanthan gum, etc.).

When present in the composition (A'), the inorganic excipient may contain metal oxides such as titanium oxides, aluminum oxides, kaolin, talc, silicates, mica and silicas.

A-very suitable excipient in the dyeing compositions according to the invention is sawdust.

The powdered composition (A') may also contain binders or coating products in an amount which preferably does not exceed approximately 3% b.w. relative to the total weight of composition (A'). These binders are preferably selected from oils and liquid fatty substances of inorganic, synthetic, animal or plant origin.

Furthermore, the present invention relates to a process of dyeing of keratin-containing fibers of the reaction products according to the present invention with autooxidable compounds and optionally further dyes.

Furthermore, the present invention relates to a process for dyeing keratin-containing fibers with the reaction products according to the present invention and capped diazotized compounds, which comprises, (a) treating the keratin-containing fibers under alkaline conditions with at least one capped diazotized compound and a coupler compound, and optionally a developer compound ad optionally an oxidizing agent, and optionally in the presence of a further dye, and optionally with at least one reaction product according to the present invention; and (b) adjusting the pH in the range of 6 to 2 by treatment with an acid, optionally in the presence of a further dye, and optionally at least one reaction product according to the present invention, with the proviso that at least in one step (a) or (b) at least one reaction product according to the present invention is present.

The capped diazotized compound and coupler compound and optionally the oxidizing agent and developer compound can be applied in any desired order successively, or simultaneously.

Preferably, the capped diazotized compound and the coupler compound are applied simultaneously, in a single composition.

"Alkaline conditions" denotes a pH in the range from 8 to 10, preferably 9.5-10, especially 9.5-10, which are achieved by the addition of bases, for example sodium carbonate, ammonia or sodium hydroxide.

The bases may be added to the hair, to the dye precursors, the capped diazotized compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

A. PREPARATION EXAMPLES

Example A1

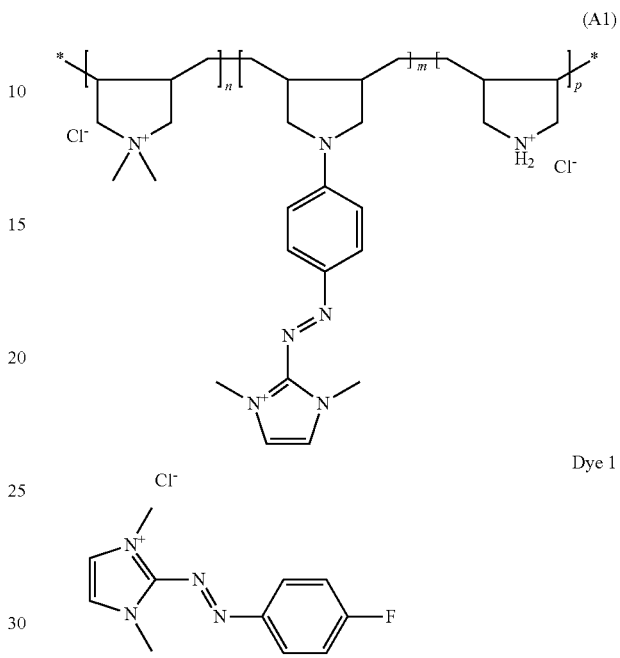

777 mg of DADMAC/DAA copolymer (4 meq. N; 50% wt DAA, Mw 7.2 k, Mn 2.6 k) are taken in 2 ml of methanol. 509 mg of azo Dye 1 were solubilized in 3 ml methanol and added to the polymer. 1,225 ml of sodium ethylate (20% in ethanol) are added over a period of 5 h and the reaction mixture was stirred further at room temperature over night. The polymer is precipitated with 15 ml of ethyl acetate, filtered and washed with 5 ml of ethyl acetate.

After drying, 1,195 g of polymer were obtained.

Example A2

Reaction of Polymer A1 with 3,3-dithiopropionic acid chloride B1

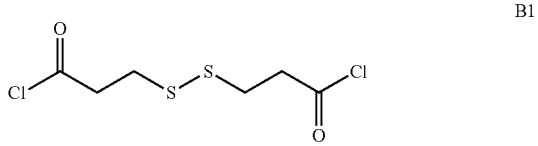 [SMILES: O=C(Cl)CCSSCCC(=O)Cl]

583 mg of Polymer A1 (3 mmeq. of free DAA) are suspended in 5 ml of dried methanol and cooled in ice/acetone. 55 mg of 3,3-dithiopropionic acid chloride B1 are added and the reaction mixture is stirred at room temperature for 2 h and an additional 15 min at 50° C. After cooling, 20 ml of acetone are added and the precipitate is filtered and washed twice with acetone. 473 mg of a dark red polymer are isolated (74% yield).

UV/VIS (water): $\lambda_{max}$=509 nm

Example A3

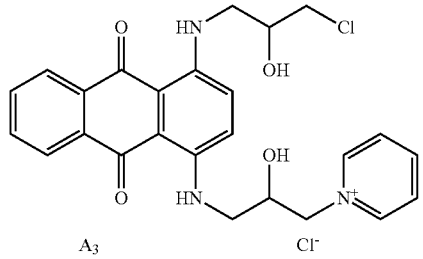

(A3)

A mixture 1.27 g of 1,4-Bis[(3-chloro-2-hydroxypropyl)amino]-9,10-anthracenedione (30 mmol) prepared as described in *J. Med. Chem.* 1992, vol. 35, n° 23, 4259-4263 in 12.7 ml of pyridine and 12.7 ml of toluene is heated at 100° C. under nitrogen atmosphere for 2 days. After cooling, the reaction mixture is evaporated to dryness and recrystallized with a mixture of dioxane and methanol (1/1).

The solid is filtered off and washed with dioxane.

After drying under vacuum, 1.08 g of a dark blue powder of formula A3 is obtained yielding 72%.

MS (ES+): m/z 465. 1H NMR (dmso-d6): δ[ppm] 10.95 (s, 1H), 9.03 (d, 2H), 8.60 (t, 1H), 8.25 (m, 2H), 8.20 (t, 2H), 7.8 (m, 2H), 7.6 (dd, 2H), 6.05-5.75, (br, 2H), 4.9 (d, 1H), 4.5 (m, 1H), 4.2 (br 1H), 3.9 (br, 1H), 3.8-3.4 (br, 6H)

Example A4

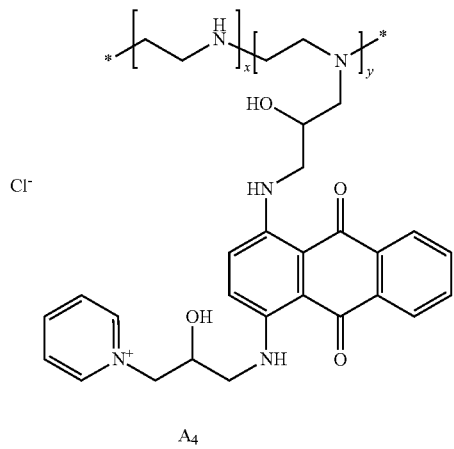

(A4)

A solution of 0.063 g of Lupasol G20 (1.47 mmol) and 0.270 g of product of formula (A3) (0.485 mmol) are reacted in 1 ml of 1-butanol at 100° C. for 2 days.

The butanol is evaporated and the reaction mixture is taken in 20 ml ethanol.

The solid is filtered off and washed with ethanol.

After drying under vacuum, 0.124 g (40%) of a dark blue powder is obtained.

1H NMR (D2O): δ[ppm] 9.0-6.4 (br, 11H), 4.2-2.4 (b, 33H)

Example A5

Reaction of Polymer (A4) with 3,3-dithiopropionylacid chloride (B1)

0.4 g of the polymer A4 are dissolved in 2 ml dichloromethane and reacted with 0.015 g 3,3-dithiopropionic acid chloride (B1) in the presence of 0.222 g triethylamine.

The reaction mixture is stirred overnight at 30° C.

After cooling the precipitate is filtered and washed with dichloromethane to give 300 mg of the polymer.

UV/VIS (water): $\lambda_{max}$=630 nm

Example A6

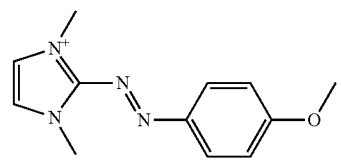

(A6$_1$)

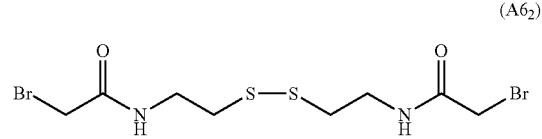

(A6$_2$)

A solution of 660 mg polyethylene imine (Lupasol FG) and 410 mg of (A6$_1$) in 35 ml isopropanol is stirred at 60° C. for 24 h.

Then 600 mg (A6$_2$) are added and the reaction mixture is stirred for another 3 h at 64° C. The resulting precipitate is collected by filtration, washed with 30 ml isopropanol and dried at room temperature to obtain 1.53 g of a dark red powder.

UV/VIS (water): $\lambda_{max}$=486 nm

Example A7

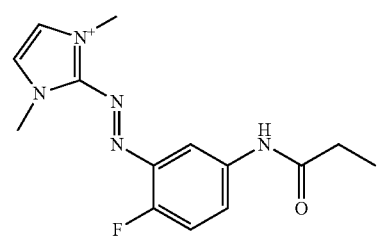

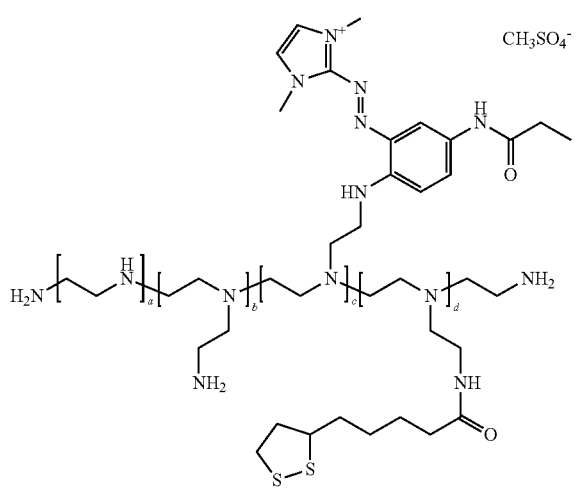

6

The synthesis of the fluoro building block 5 is described in the patent WO2006136617.

0.215 g of Lupasol PR8515 are solubilized in 5 ml of 2-propanol. A solution of 0.4 g of compound 5 (MW 401.1) in 10 ml of methanol is added to the polymer solution and stirred for 2 hour at 40° C. In a second flask, 0.155 g of thionyl chloride are added at room temperature to a suspension of 0.206 g of lipoïc acid in 5 ml dichloromethane. After 30 minutes stirring this solution is added to the polymer mixture and stirred for 3 hours at room temperature. The reaction mixture is then diluted with 50 ml of ethylacetate and is left to decantate. The sticky product is solubilised in methanol and evaporated to dryness giving 520 mg of a sticky dark blue compound.

$^1$H NMR (D$_2$O): δ [ppm] 8.1 (br), 7.8 (br), 7.4 (br), 6.9 (br), 4.1-2.7 (br), 2.3 (br)

UV/VIS (acetonitril): $\lambda_{max}$=556 nm

Example A8

Same procedure as in example A7 but with Lupasol FG as polymer.

$^1$H NMR (D$_2$O): δ [ppm] 8.0 (br), 7.8 (br), 7.4 (br), 6.9 (br), 4.0-2.7 (br), 2.4 (br)

UV/VIS (acetonitril): $\lambda_{max}$=558 nm

Example A9

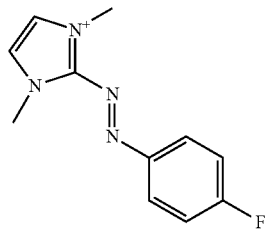

7

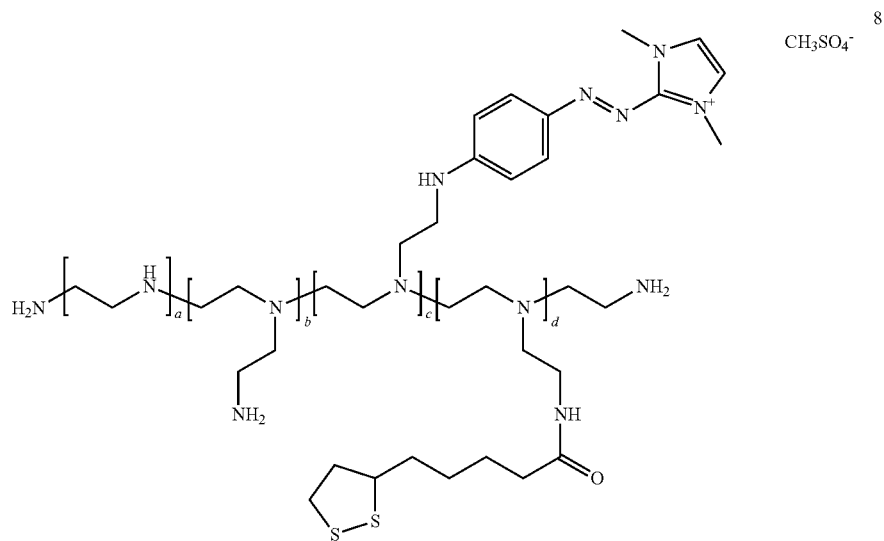

8

The dye building blocks of formula 7 is disclosed in WO 2006/136617 and can be used to prepare the polymeric dye 8 following the same procedure described in example 7 with Lupasol FG and compound 7.

$^1$H NMR (D$_2$O): δ [ppm] 7.6 (br), 7.2 (br), 6.6 (br), 4.0-2.6 (br)

UV/VIS (water): $\lambda_{max}$=488 nm

B. APPLICATION EXAMPLES

In the following application examples compositions within the below given definitions are used:

Solution 1 (Permanent Lotion, pH 8.2)

Aqua, Ammonium Thioglycolate, Ammonium Bicarbonate, Ethoxydiglycol, Hexylene Glycol, Thioglycolic Acid; Thiolactic Acid, PEG-60 Hydrogenated Castor Oil, Glycine, Etidronic Acid, Isoceteth-20, Polysilicone-9, Styrene/PVP Copolymer, Trideceth-12, Amodimethicone, Cetrimonium Chloride, Ammonium Hydroxide, Polyquaternium-6, Isopropyl Alcohol, Alcohol denat., Simethicone, Perfume Solution 2 (Permanent Fixation, pH 3.9)

Based on:

Aqua, Hydrogen Peroxide, Propylene Glycol, Lauryldimonium Hydroxypropyl Hydrolyzed Wheat Protein, PEG-5 Cocamide, Sodium Cocoamphoacetate, Polyquaternium-35, CocoBetaine, Acetaminophen, Phosphoric Acid, Sodium Chloride, Perfume

Example B1

0.2% (abs.) of the dye A2 is dissolved in a 5% solution of a non-ionic surfactant (Plantacare 200UP, Henkel) adjusted to pH 9.5 using citric acid and monoethanolamine.

This red dyeing solution is applied on the dry hair (two blond, two middle blond and two damaged hair strands) and allowed to stand for 20 min. at room temperature. Then, the strands are rinsed under tap water and dried 12 hours.

Example B2

A solution 1 (permanent lotion) is applied on shampooed hair (two blond, two middle blond, and two damaged hair strands) and allowed to stand for 10 min. Then, the strands are rinsed under tap water, and the towel dry strands are treated with the 0.2%, by weight colouring material solution of example B1 allowed to stand for 20 min and then rinsed. Then, the towel dry strands are treated with the solution 2 (permanent fixation) and allowed to stand for 10 min. Then the strands are rinsed under tap water and dried 12 hours at room temperature.

Example B3

0.2% (abs.) (63.5 mg) of the dye A5 with a dye assay of 78.7%) is dissolved in 25 g of a 5% solution of a non-ionic surfactant (Plantacare 200UP, Henkel) adjusted to pH 9.5 using citric acid and monoethanolamine.

This blue dyeing solution is applied on the dry hair (two blond, two middle blond and two damaged hair strands) and allowed to stand for 20 min. at room temperature. Then, the strands are rinsed under tap water and dried 12 hours.

Example B4

A solution 1 (permanent lotion) is applied on shampooed hair (two blond, two middle blond, and two damaged hair strands) and allowed to stand for 10 min. Then, the strands are rinsed under tap water, and the towel dry strands are treated with the 0.2%, by weight colouring material solution of example B3 allowed to stand for 20 min and then rinsed. Then, the towel dry strands are treated with the solution 2 (permanent fixation) and allowed to stand for 10 min. Then the strands are rinsed under tap water and dried 12 hours at room temperature.

Example B5

0.2% (abs.) (145 mg) of the dye A6 with a dye assay of 24.5% is dissolved in 17.8 g of a 20% solution of urea adjusted to pH 9.5 monoethanolamine.

This red dyeing solution is applied on the dry hair (two blond, two middle blond and two damaged hair strands) and allowed to stand for 20 min. at room temperature. Then, the strands are rinsed under tap water and dried 12 hours.

Example B6

A solution 1 (permanent lotion) is applied on shampooed hair (two blond, two middle blond, and two damaged hair strands) and allowed to stand for 10 min. Then, the strands are rinsed under tap water, and the towel dry strands are treated with the 0.2%, by weight colouring material solution of example B5 allowed to stand for 20 min and then rinsed. Then, the towel dry strands are treated with the solution 2 (permanent fixation) and allowed to stand for 10 min. Then the strands are rinsed under tap water and dried 12 hours at room temperature.

| Assay | substance color | hair type | color | intensity | brilliance | dE* washing fastness 10x washed with shampoo | comment |
|---|---|---|---|---|---|---|---|
| (A2) | red | blond | red | good | good | 8.7 | Example B1 |
| | | middle blond | red | good | good | 4.2 | Example B1 |
| | | bleached | red | good | good | 5.4 | Example B1 |
| | | | | | | | Example B1 |
| | | gray 90% | red | good | good | 6.5 | Example B1 |
| | | blond | red | good | good | 7.3 | Example B2 |
| | | middle blond | red | good | good | 2.6 | Example B2 |
| | | bleached | red | good | good | 5.4 | Example B2 |
| | | gray 90% | red | good | good | 6.0 | Example B2 |
| A5 | blue | blond | blue | bad | bad | 12.0 | Example B3 |
| | | middle | blue | bad | bad | 9.1 | Example B3 |

-continued

| Assay | substance color | hair type | color | intensity | brilliance | dE* washing fastness 10x washed with shampoo | comment |
|---|---|---|---|---|---|---|---|
| | | blond bleached | blue | good | good | 22.2 | Example B3 |
| | | gray 90% | blue | bad | bad | 10.6 | Example B3 |
| | | blond | blue | moderate | moderate | 6.7 | Example B4 |
| | | middle blond | blue | bad | bad | 7.1 | Example B4 |
| | | bleached | blue | good | good | 16.4 | Example B4 |
| | | gray 90% | blue | moderate | moderate | 6.0 | Example B4 |
| A6 | red | blond | red | good | good | 4 | Example B5 |
| | | middle blond | red | good | good | 5.1 | Example B5 |
| | | bleached | red | good | good | 10.8 | Example B5 |
| | | blond | red | good | good | 2.2 | Example B6 |
| | | middle blond | red | good | good | 4.2 | Example B6 |
| | | bleached | red | good | good | 9.7 | Example B6 |

Mixtures of Polymeric Dyes (Ex. B7-B16)
A die emulsion, pH=10.5

| INGREDIENT | w/w % |
|---|---|
| Mixture of dyes as described in table 4 and 5 | X |
| Cetearyl Alcohol | 12.00 |
| Ceteareth-20 | 4.50 |
| Polysorbate 60 | 2.30 |
| Glyceryl Stearate SE | 2.00 |
| Sorbitan Stearate | 0.75 |
| Oleth-5 | 1.25 |
| Caprylic/Capric Triglyceride | 0.50 |
| Disodium EDTA | 0.05 |
| Monoethanolamine 99% | 0.90 |
| Ammonium Hydroxide 29% | 6.60 |
| Dihydroxypropyl PEG-5 Linoleammonium Chloride | 0.50 |
| Hydrolyzed Soy Protein 20% | 0.50 |
| Fragrance Drom 847 735 - Day at the Beach | 0.50 |
| Deionized Water 70° C. | ad 100.00 | is mixed with 1.5 wt. % of a 9% hydrogen peroxide solution and the mixture is immediately applied to a tress of brown hair.

After 30 minutes the tress is rinsed, shampooed, rinsed and dried.

The color of the dyed tresses is given in Tables 4 and 5.

TABLE 4

Mixtures of polymeric dyes

| Comp. of formula | Color | B7 | B8 | B9 | B10 |
|---|---|---|---|---|---|
| A6 | red | 0.5 | 0.3 | 0.01 | 0.03 |
| A24-UK2440219[4)] | yellow | 5.0 | | | 0.03 |
| A23-EP2007/056945[2)] | orange | | 0.4 | 0.07 | |
| A15-WO09/090124[3)] | blue | | | | 0.03 |
| A20-WO09/090124[3)] | blue | 2.0 | | | |
| A23-WO09/090124[3)] | blue | | 0.1 | | |
| A40-WO09/090124[3)] | blue | | | | 0.03 |
| Total dye content X | | 7.5 | 0.8 | 0.11 | 0.09 |
| Color result on bleached hair[1)] | | B | B | B | B |

[1)]S = black, B = brown
[2)]Polymeric dyes described in patent application no. EP2007/056945.
[3)]Polymeric dyes described in patent application no. WO09/090124
[4)]Polymeric dyes described in patent application no. UK24400219

TABLE 5

Mixtures of polymeric dyes and direct dyes

| Comp. of formula | Formulation No.: B11 | B12 | B13 | B14 | B15 | B16 |
|---|---|---|---|---|---|---|
| A6 | 0.2 | 0.5 | 0.1 | 0.2 | 0.3 | 0.1 |
| Direct Dye | | | | | | |
| C.I. Basic Blue 99 | | 2.0 | | 0.2 | 1.6 | 0.2 |
| C.I. Basic Blue 124 | 0.1 | | 0.5 | | | |
| Basic Yellow 87 | | 5.0 | | | 2.0 | |
| HC Red No. 3 | | | | | 0.1 | |
| HC Red BN | | | | | 0.1 | |
| Basic Brown 16 | 0.1 | | | | | |
| Basic Brown 17 | 0.1 | | | | 2.0 | 0.5 |
| Total dye content X | 0.5 | 7.5 | 0.6 | 0.4 | 0.5 | 0.8 |
| Color result on bleached hair[1)] | B | B | V | V | S | B |

[1)]S = black, B = brown, V = violet, G = green

In the following examples the abbreviation RKN is a designation of grade and indicates the purity of the cellulose; the abbreviation SR (Schopper-Riegler) indicates the freeness.

Example B17

50 parts of chemically bleached beech sulfite are mixed with 50 parts of bleached RKN 15 (freeness 22 DEG SR) and 2 parts of the dye according to Example A1 in water (pH 6, hardness of water 10 DEG of German hardness, temperature 20 DEG and liquor ratio 40:1). After stirring for 15 minutes, paper sheets are produced on a Frank sheet-former. The paper has been dyed in a very intense red shade. The effluent is completely colourless. A degree of exhaustion of virtually 100 percent is attained. The fastness properties to light and wet processing are excellent.

Example B18

A paper web composed of bleached beech sulfite pulp (22 DEG SR) is produced on a continuously operating laboratory paper-making machine. An aqueous solution of the dye according to Example A6 is metered continuously into the low-density pulp 10 seconds upstream of the head box, with vigorous turbulence (0.5 percent dyeing, liquor ratio 400:1, hardness of water 10 DEG German hardness, pH 6, temperature 20 DEG).

A deep red coloration of medium intensity is formed on the paper web. The effluent is completely colourless.

Example B19

10 parts of cotton fabric (bleached, mercerized cotton) are dyed in a laboratory beam dyeing machine in 200 parts of a liquor (hardness of water 10 DEG German hardness, pH 4, dye liquor circulated three times per minute) containing 0.05 part of the dye according to Example A4. The temperature is raised in the course of 60 minutes from 20 DEG to 100 DEG and is then kept constant for 15 minutes.

The dye liquor is completely exhausted. A deep blue coloration distinguished by good fastness to light and very good fastness to wet processing is formed on the cotton fabric.

A textile fabric composed of regenerated (viscose) is dyed by the same procedure. A deep blue dyeing which has good fastness to light and very good fastness to wet processing is also obtained on this material by means of the dye of Example A4.

Example B20 of a Purely Solvent-containing Wood Stain:
3.0 parts by weight of the dye A1
40.0 parts by weight of ethyl alcohol,
40.0 parts by weight of 1 methoxy-2-propanol and
17.0 parts by weight of isopropanol Example B21 of an Aqueous Wood Stain:
3.0 parts by weight of the dye A6 are dissolved in 100.0 ml of water containing 0.05 percent by weight Invadin LU (a wetting agent).

The wood stains obtained according to the above Examples are applied by means of a brush to a 10.times.5.5 cm piece of ash wood. The coloured piece of wood is dried in air for 12 hours.

The invention claimed is:
1. The reaction product of
(A) a polymeric backbone selected from the compounds of the formulas

(A$_1$)

with
(B) a chromophore selected from the compounds of formulas

  (B$_1$)

  (B$_2$)

and

,  (B$_3$)

wherein
T, U and Q independently from each other, represent repeating units of a polymer backbone;
X$_1$, X$_2$ and X$_3$ independently from each other are the direct bond; an optionally substituted, saturated or unsaturated, fused or non-fused aromatic or nonaromatic (heterocyclic) bivalent radical optionally comprising at least one heteroatom; a saturated or unsaturated, fused or non-fused aromatic or nonaromatic bivalent radical comprising at least one heteroatom, which is optionally substituted by C$_1$-C$_{30}$alkyl, C$_1$-C$_{30}$alkoxy, C$_2$-C$_{12}$alkenyl, C$_5$-C$_{10}$aryl, C$_5$-C$_{10}$cycloalkyl, C$_1$-C$_{10}$alkyl(C$_5$-C$_{10}$arylene), hydroxy or halogen; or a bivalent radical of formula

 (B$_a$)

wherein
V is straight-chain or branched —C$_1$-C$_{12}$alkylene; —C$_2$-C$_{12}$alkenylene-; C$_5$-C$_{10}$cycloalkylene; C$_5$-C$_{10}$arylene; C$_5$-C$_{10}$arylene-(C$_1$-C$_{10}$)alkylene-; —C(O)—; —(CH$_2$CH$_2$—O)$_{1-5}$—; —(CH$_2$CH$_2$CH$_2$—O)$_{1-5}$—; —C(O)O—; —OC(O)—; —N(R$_1$)—; —CON(R$_2$)—; —(R$_1$)NC(O)—; —O—; —S—; —S(O)—; —S(O)$_2$—; —S(O)$_2$N(R$_1$)—; or —N$^+$(R$_1$)(R$_2$)—;
Z is a biradical of formula

 (B$_b$)

 (B$_c$)

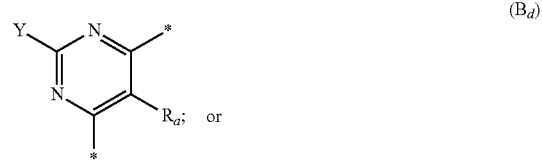 (B$_d$)

 (B$_e$)

R$_1$ and R$_2$ independently from each other are hydrogen; C$_1$-C$_6$alkyl; C$_1$-C$_6$alkoxy; C$_1$-C$_6$-alkylamino; C$_6$-C$_{10}$aryloxy; or C$_6$-C$_{10}$arylamino;
R$_a$ is hydrogen; C$_1$-C$_6$alkyl; C$_1$-C$_6$-alkoxy; C$_1$-C$_6$-alkylamino; C$_6$-C$_{10}$aryloxy; C$_6$-C$_{10}$-arylamino; SO$_2$R$_5$; chlorine; or fluorine;
Y is R$_a$, Y$_1$, Y$_2$ or Y$_3$;
Y$_1$, Y$_2$ and Y$_3$ independently from each other are a residue of an organic dye;
G represents a functional group capable of reacting with the polymeric backbone (A) selected from halide, activated methoxy, hydroxy, tosylate, mesylate, carboxylic acid, carboxylic acid chloride, carboxylic ester, sulfonyl chloride, vinyl sulfone, acrylate, isocyanate, epoxide, anhydride, primary, secondary or tertiary amines and hydroxy;
m is a number from 0 to 50000;
n is a number from 0 to 50000; and
p is a number from 1 to 50000;
m and n independently from each other are 0, or 1;
wherein the sum of m+n+p≥3;

t and u independently from each other are 1, or 2;
and with
(C) at least one sulfide containing compound of formula $$G\text{-}(Z_1)_r\text{-}X_3\text{-}S\text{-}Z_3\text{-}[X_4\text{-}(Z_2)_q\text{-}G_1]_s, \quad (C_1)$$

or $$G\text{-}(Z_1)_r\text{-}X_5; \quad (C_2)$$

wherein
$X_3$ and $X_4$ each independently from each other are unsubstituted or substituted, straight-chain or branched, interrupted or uninterrupted —$C_1$-$C_{10}$alkylene-; —$C_5$-$C_{10}$cycloalkylene-; $C_5$-$C_{10}$arylene; or —$C_5$-$C_{10}$arylene-($C_1$-$C_{10}$alkylene)-;
$X_5$ is a 5 to 7 membered heterocyclic ring containing a disulfide (S—S) bond
$Z_1$ and $Z_2$ independently from each other are —C(O)—; —$C_2$-$C_{12}$alkenylene-; —(CH$_2$CH$_2$—O)$_{1\text{-}5}$—; —$C_1$-$C_{10}$alkylene($C_5$-$C_{10}$arylene)-; —$C_5$-$C_{10}$arylene-; —$C_5$-$C_{10}$cycloalkylene-; —C(O)O—; —OCO—; —N(R$_3$)—;

$$-\underset{\underset{R_4}{|}}{\overset{\overset{R_3}{|}}{N^+}}-;$$

—CON(R$_4$)—; —(R$_5$)NC(O)—; —CH$_2$C(O)N(R$_6$)—; —(R$_6$)NC(O)CH$_2$—; —O—; —S—; —S(O)—; or —S(O)$_2$—;
$R_3$, $R_4$, $R_5$ and $R_6$ independently from each other are hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);
$G_1$ is hydrogen; or represents a functional group capable of reacting with the polymeric backbone (A) selected from halide, activated methoxy, hydroxy, tosylate, mesylate, carboxylic acid, carboxylic acid chloride, carboxylic ester, sulfonyl chloride, vinyl sulfone, acrylate, epoxide and anhydride;
q, r and s independently from each other are 0 or 1;
if s is 0,
$Z_3$ is hydrogen; SR$_7$; or a group of formula $$\overset{V}{\underset{W,}{*\diagup\diagdown}} \quad (C_a)$$

wherein
$R_7$ is hydrogen; $C_1$-$C_{12}$alkyl; $C_6$-$C_{12}$aryl; or $C_6$-$C_{12}$aryl-$C_1$-$C_{12}$alkyl; or a radical of formula —(CH$_2$)$_v$—R$_8$;
$R_8$ is a radical of formula —NH—(CO)—R$_9$; —(CO)—R$_9$; —NR$_9$R$_{10}$; or OH;
$R_9$ and $R_{10}$ independently of each other are hydrogen; hydroxy; $C_1$-$C_5$alkyl; or $C_1$-$C_5$alkoxy; and
v is a number from 1 to 4; and
wherein the —(CH$_2$)$_v$-groups are optionally substituted by one or more than one —NR$_{11}$R$_{12}$ or —OR$_{12}$ groups, wherein
$R_{11}$ or $R_{12}$ independently of another are hydrogen; or $C_1$-$C_5$alkyl;

V is hydrogen; $C_1$-$C_{12}$alkyl; $C_6$-$C_{12}$aryl; $C_6$-$C_{12}$aryl-$C_1$-$C_{12}$alkyl; —OR$_{13}$; —NR$_{13}$R$_{14}$, or —SR$_{13}$;
W is O; S; or N—R$_{15}$;
$R_{13}$, $R_{14}$ and $R_{15}$ independently from each other are hydrogen; $C_1$-$C_{12}$alkyl; $C_6$-$C_{12}$aryl; $C_6$-$C_{12}$aryl-$C_1$-$C_{12}$alkyl;
if s is 1,
$Z_3$ is —S—;
wherein the polymeric backbone (A) can be reacted either first with the sulfide containing compound (C) and then with the chromophore (B); or first with the chromophore (B) and then with the sulfide containing compound (C); or the polymeric backbone (A) can be reacted simultaneously with the chromophore (B) and with the sulfide containing compound (C).

2. Reaction product according to claim 1, which comprises the reaction product of
(A) a polymeric backbone selected from the compounds of the formulas $$*-[-T-]_n-[-U-]_m-[-Q-]_p-* \quad (A)$$

(B) a chromophore selected from the compounds of formulas $$G\text{-}X_1Y_1; \quad (B_1)$$

$$G\text{-}X_2Y_2; \quad (B_2)$$

and $$G\text{-}X_3Y_3 \quad (B_3)$$

wherein
T, U and Q independently from each other, represent repeating units of a polymer backbone;
$X_1$, $X_2$ and $X_3$ independently from each other are the direct bond; an optionally substituted, saturated or unsaturated, fused or non-fused aromatic or nonaromatic (heterocyclic) bivalent radical optionally comprising at least one heteroatom; a saturated or unsaturated, fused or non-fused aromatic or nonaromatic bivalent radical comprising at least one heteroatom, which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), hydroxy or halogen; or a bivalent radical of formula $$-(V)_t(Z)_u-, \quad (B_a)$$

wherein
V is straight-chain or branched —$C_1$-$C_{12}$alkylene; —$C_2$-$C_{12}$alkenylene-; $C_5$-$C_{10}$cycloalkylene; $C_5$-$C_{10}$arylene; $C_5$-$C_{10}$arylene-($C_1$-$C_{10}$)alkylene-; —C(O)—; —(CH$_2$CH$_2$—O)$_{1\text{-}5}$—; —(CH$_2$CH$_2$CH$_2$—O)$_{1\text{-}5}$—; —C(O)O—; —OC(O)—; —N(R$_1$)—; —CON(R$_2$)—; —(R$_1$)NC(O)—; —O—; —S—; —S(O)—; —S(O)$_2$—; —S(O)$_2$N(R$_1$)—; or —N$^+$(R$_1$)(R$_2$)—;
Z is a biradical of formula $$\text{[triazine ring structure with substituents *, *, Y]} \quad (B_b)$$

-continued

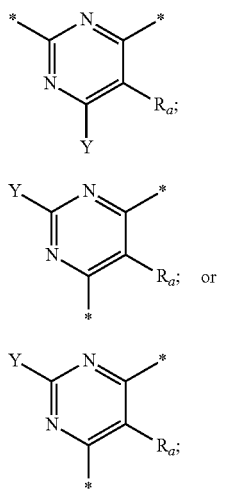

(B<sub>c</sub>)

(B<sub>d</sub>)

(B<sub>e</sub>)

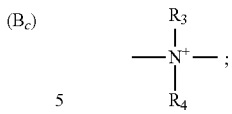

(B<sub>c</sub>)

—CON(R$_4$)—; —(R$_5$)NC(O)—; —CH$_2$C(O)N(R$_6$)—; —(R$_6$)NC(O)CH$_2$—; —O—; —S—; —S(O)—; or —S(O)$_2$—;

R$_3$, R$_4$, R$_5$ and R$_6$ independently from each other are hydrogen; unsubstituted or substituted, straight-chain or branched, monocyclic or polycyclic, interrupted or uninterrupted C$_1$-C$_{14}$alkyl; C$_2$-C$_{14}$alkenyl; C$_6$-C$_{10}$aryl; C$_6$-C$_{10}$aryl-C$_1$-C$_{10}$alkyl; or C$_5$-C$_{10}$alkyl(C$_5$-C$_{10}$aryl);

G$_1$ is hydrogen; or represents a functional group capable of reacting with the polymeric backbone (A) selected from halide, activated methoxy, hydroxy, tosylate, mesylate, carboxylic acid, carboxylic acid chloride, carboxylic ester, sulfonyl chloride, vinyl sulfone, acrylate, epoxide and anhydride;

q, r and s independently from each other are 0 or 1;

if s is 0,

Z$_3$ is hydrogen or a group of formula

(C$_a$)

R$_1$ and R$_2$ independently from each other are hydrogen; C$_1$-C$_6$alkyl; C$_1$-C$_6$alkoxy; C$_1$-C$_6$-alkylamino; C$_6$-C$_{10}$aryloxy; or C$_6$-C$_{10}$arylamino;

R$_a$ is hydrogen; C$_1$-C$_6$alkyl; C$_1$-C$_6$-alkoxy; C$_1$-C$_6$-alkylamino; C$_6$-C$_{10}$aryloxy; C$_6$-C$_{10}$-arylamino; SO$_2$R$_5$; chlorine; or fluorine;

Y is R$_a$, Y$_1$, Y$_2$ or Y$_3$;

Y$_1$, Y$_2$ and Y$_3$ independently from each other are a residue of an organic dye;

G represents a functional group capable of reacting with the polymeric backbone (A) selected from halide, activated methoxy, hydroxy, tosylate, mesylate, carboxylic acid, carboxylic acid chloride, carboxylic ester, sulfonyl chloride, vinyl sulfone, acrylate, isocyanate, epoxide, anhydride, primary, secondary or tertiary amines and hydroxy;

m is a number from 0 to 50000;
n is a number from 0 to 50000; and
p is a number from 1 to 50000;
m and n independently from each other are 0, or 1;
wherein the sum of m+n+p≥3;
t and u independently from each other are 1, or 2;
and with (C) at least one sulfide containing compound of formula

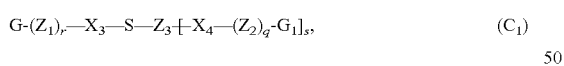

(C$_1$)

or

(C$_2$)

wherein

X$_3$ and X$_4$ each independently from each other are unsubstituted or substituted, straight-chain or branched, interrupted or uninterrupted —C$_1$-C$_{10}$alkylene-; —C$_5$-C$_{10}$cycloalkylene-; C$_5$-C$_{10}$arylene; or —C$_5$-C$_{10}$arylene-(C$_1$-C$_{10}$alkylene)-;

X$_5$ is a 5 to 7 membered heterocyclic ring containing a disulfide (S—S) bond

Z$_1$ and Z$_2$ independently from each other are —C(O)—; —C$_2$-C$_{12}$alkenylene-; —(CH$_2$CH$_2$—O)$_{1-5}$—; —C$_1$-C$_{10}$alkylene(C$_5$-C$_{10}$arylene)-; —C$_5$-C$_{10}$arylene-; —C$_5$-C$_{10}$cycloalkylene-; —C(O)O—; —OCO—; —N(R$_3$)—;

wherein

V is hydrogen; C$_1$-C$_{12}$alkyl; C$_6$-C$_{12}$aryl; C$_6$-C$_{12}$aryl-C$_1$-C$_{12}$alkyl; —OR$_7$; —NR$_8$R$_9$, or —SR$_{10}$;

W is O; S; or N—R$_{11}$;

R$_7$, R$_8$, R$_9$, R$_{10}$ and R$_{11}$ independently from each other are hydrogen; C$_1$-C$_{12}$alkyl; C$_6$-C$_{12}$aryl; or C$_6$-C$_{12}$aryl-C$_1$-C$_{12}$alkyl;

if s is 1,

Z$_3$ is —S—;

wherein the polymeric backbone (A) can be reacted either first with the sulfide containing compound (C) and then with the chromophore (B); or first with the chromophore (B) and then with the sulfide containing compound (C); or the polymeric backbone (A) can be reacted simultaneously with the chromophore (B) and with the sulfide containing compound (C).

3. Reaction product according to claim 1, wherein
Y$_1$, Y$_2$ and Y$_3$ are a residue of a cationically charged organic dye.

4. Reaction product according to claim 1, wherein
Y$_1$, Y$_2$ and Y$_3$ independently from each other are selected from the group of anthraquinone, acridine, azo, disazo, trisazo, azamethine, hydrazomethine, triphenylmethane, benzodifuranone, coumarine, diketopyrrolopyrrol, oxazine, dioxazine, diphenylmethane, formazane, indigoid indophenol, naphthalimide, naphthoquinone, nitroaryl, merocyanine, methine oxazine, perinone, perylene, pyrenequinone, phtalocyanine, phenazine, fluorindine, quinoneimine, quinacridone, quinophtalone, styryl, stilbene, xanthene, thiazine and thioxanthene dyes.

5. Reaction product according to claim 1, wherein
Y$_1$, Y$_2$ and Y$_3$ independently from each other are selected from anthraquinone, azo, azomethine, hydrazomethine, merocyanine, methine, oxazine and styryl dyes.

6. Reaction product according to claim 4, wherein $Y_1$, $Y_2$ and $Y_3$ have the same meaning.

7. Reaction product according to claim 1, wherein
T, U and Q, independently from each other are selected from polyethylenimine, polypropyleneimine, polyvinylamine; polyvinylimine; polysiloxane; polystyrene, polyvinylimidazol, polyvinylpyridine, DADMAC/DAA copolymers, polyetheramines, polyvinylalcohol, polyacrylate, polymethacrylate; polyureas, polyurethanes derived from hydroxyl-terminated polyethers, polyesters or polybutadienes on the one hand and aliphatic or aromatic polyisocyanates on the other, as well as precursors thereof; polyamides and copolyamides derived from diamines and dicarboxylic acids and/or from aminocarboxylic acids or the corresponding lactams; functionalized polysaccharide, starch, cellulose and lignin and copolymers and blends of the mentioned polymers.

8. Reaction product according to claim 1, wherein the molecular weight of the polymeric dye is from 400 to $2*10^6$.

9. Reaction product according to claim 1, wherein the sulfide containing compound (C) corresponds to formula $$G\text{-}(Z_1)_r\text{—}X_3\text{—}S\text{—}S\text{—}X_4\text{—}(Z_2)_q\text{-}G, \quad (C_3)$$

wherein
$Z_1$, $Z_2$, $X_3$, $X_4$, G, q and r are defined as in claim 1.

10. Reaction product according to claim 1, wherein the sulfide containing compound (C) corresponds to formula $$G\text{—}(Z_1)_r\text{—}X_3\text{—}S\text{—}H; \quad \text{or} \quad (C_4)$$

$$\underset{R_{12}}{G\diagdown N}\diagdown X_3\diagdown S\diagup Z_3; \quad (C_5)$$

wherein
$R_{12}$ is hydrogen; $C_1$-$C_{12}$alkyl; or phenyl-$C_1$-$C_4$alkyl; and
$Z_3$ is hydrogen; or a group of formula ($C_a$) as defined in claim 1; and
$Z_1$, $X_3$, G and r are defined as in claim 1.

11. Reaction product according to claim 1, wherein the sulfide containing compound (C) corresponds to formula $$G\text{—}(Z_1)_r\diagdown\underset{S}{\overset{S}{\diagup}}, \quad (C_6)$$

wherein
$Z_1$, G and r are defined as in claim 1.

12. Reaction product according to claim 1, which corresponds to the reaction product of formula $(A_1\text{-}B_1)$ with the sulfide containing compound $(C_3)$ G-$(Z_1)_r$—$X_3$—S—S—$X_4$—$(Z_2)_q$-G, wherein
$X_1$ is as described in Formula B1
$Y_1$ is a residue of an organic dye selected from azo, disazo, azomethine, hydrazomethine, merocyanine, methine, oxazine and styryl dyes;
m and n are a number from 0 to 50000; wherein the sum of m and n≥3; and
$Z_1$, $Z_2$, $X_3$, $X_4$, G, q and r are defined as in claim 1.

13. Reaction product according to claim 1, which corresponds to the reaction product of formula $(A_2\text{-}B_2)$ with the sulfide containing compound $$G\text{-}(Z_1)_r\text{—}X_3\text{—}S\text{—}S\text{—}X_4\text{—}(Z_2)_q\text{-}G, \quad (C_3)$$

wherein
$X_1$ is as described in Formula B1
$Y_1$ is a residue of an organic dye selected from azo, disazo, azomethine, hydrazomethine, merocyanine, methine, oxazine and styryl dyes;
m, n and p are a number from 0 to 50000; wherein the sum of m, n and p≥3; and
$Z_1$, $Z_2$, $X_3$, $X_4$, G, q and r are defined as in claim 1.

14. A composition for dyeing organic material selected from leather, silk, cellulose or polyamides and natural and synthetic fibers comprising at least one reaction product as defined in claim 1.

15. Composition according to claim 14, wherein the organic material is a keratin-containing fibre.

16. A hair dye composition according to claim 15 comprising in addition at least one single further direct dye, polymeric dye and/or an oxidative dye.

17. A hair dye composition according to claim 15 in form of a shampoo, a conditioner, a gel or an emulsion.

18. Method of dyeing organic material selected from leather, silk, cellulose or polyamides and natural and synthetic fibers comprising treating the organic material with at least one reaction product as defined in claim 1.

19. A method according to claim 18 wherein the dyeing with the compounds of formula (1) is carried out in the presence of a reduction agent.

20. A method according to claim 19, wherein the reducing agent is selected from thioglycol acid or salts thereof, glycerin monothioglycolate, cystein, 2-mercaptopropionic acid, 2-mercaptoethylamine, thiolactic acid, thioglycerine, sodium sulfite, dithionithe, ammonium sulfite, sodium bisulfite, sodium metabisulfite and hydrochinon.

21. A method of dyeing organic material selected from leather, silk, cellulose or polyamides and natural and synthetic fibers, comprising treating the organic material
a) optionally with a reduction agent, and
b) at least one of the reaction product as defined in claim 1, and
c) optionally with an oxidizing agent.

22. A method according to claim 18, wherein the organic material is wool, leather, textiles, paper or wood.

23. A method for dyeing keratin-containing fibers, comprising
 a) dyeing the keratin-containing fiber with at least one of the reaction product as defined in claim 1,
 b) wearing the coloured keratin-containing fiber for the desired period of time, and
 c) removing the colour applied in step a) from hair by contacting the hair with an aqueous based colour removal composition containing a reducing agent capable of disrupting the —S—S-bonds between the dye molecule and the hair fiber surface to cause the dye molecule to become disassociated from the fiber.

\* \* \* \* \*